United States Patent [19]

Miyazawa et al.

[11] Patent Number: 5,714,088
[45] Date of Patent: Feb. 3, 1998

[54] LIQUID CRYSTALLINE COMPOUND HAVING BRANCHED ALKYL GROUP AT ITS SIDE CHAIN AND LIQUID CRYSTAL COMPOSITION CONTAINING THE SAME

[75] Inventors: Kazutoshi Miyazawa; Shuichi Matsui; Yasuko Sekiguchi; Etsuo Nakagawa, all of Chiba, Japan

[73] Assignee: Chisso Corporation, Osaka-fu, Japan

[21] Appl. No.: 620,181

[22] Filed: Mar. 22, 1996

[30] Foreign Application Priority Data

Mar. 23, 1995 [JP] Japan .................. 7-090278

[51] Int. Cl.$^6$ .................. C09K 19/30; C09K 19/52; G02F 1/13; C07C 25/13
[52] U.S. Cl. .................. 252/299.63; 252/299.01; 252/299.66; 349/182; 570/127; 570/131
[58] Field of Search .................. 252/299.01, 299.63, 252/299.66; 349/182; 570/127, 131

[56] References Cited

FOREIGN PATENT DOCUMENTS

| | | |
|---|---|---|
| 4326269 | 2/1995 | Germany . |
| 4-501864 | 4/1992 | Japan . |
| WO91/03446 | 3/1991 | WIPO . |

OTHER PUBLICATIONS

CA 123:242169, 1995.
Patent Abstracts of Japan, vol. 16, No. 470 (C-0990), Sep. 30, 1992, & JP-A-04 169541.

Primary Examiner—Shean C. Wu
Attorney, Agent, or Firm—Wenderoth, Lind & Ponack

[57] ABSTRACT

Liquid crystalline compounds are disclosed which are expressed by the following general formula (1)

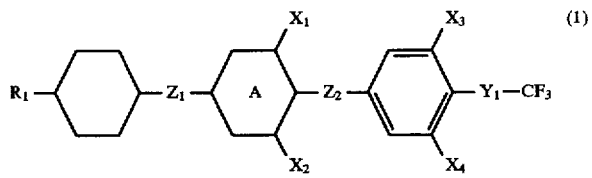

wherein $R_1$ represents a branched alkyl group having 3 to 10 carbon atoms, ring A represents 1,4-phenylene group or 1,4-cyclohexylene group, $Z_1$ and $Z_2$ independently represent a single bond or 1,2-ethylene group, respectively, $X_1$, $X_2$, $X_3$, and $X_4$ independently represent fluorine atom or hydrogen atom, respectively, and $Y_1$ represents oxygen atom or a single bond. The compounds are excellent in compatibility with other liquid crystalline compounds, and have a large positive value of dielectric anisotropy, extremely low viscosity, extremely high specific resistance (high voltage holding ratio), and excellent UV stability.

13 Claims, No Drawings

LIQUID CRYSTALLINE COMPOUND HAVING BRANCHED ALKYL GROUP AT ITS SIDE CHAIN AND LIQUID CRYSTAL COMPOSITION CONTAINING THE SAME

BACKGROUND OF THE INVENTION

1. Field of the Invention

The present invention is to provide a novel liquid crystalline compound which exhibits several kinds of physical properties suitable material for electrooptical display, to provide a liquid crystal composition having the novel liquid crystalline compound and exhibiting several suitable physical properties, and to provide a liquid crystal display device having the liquid crystal composition. More specifically, the present invention is to provide a liquid crystalline compound and liquid crystal composition having characteristics suitable for use in an active matrix driving mode LCD, particularly for TFT mode LCD.

2. Description of the Prior Art

Liquid crystal display devices are used for watches, tabletop calculators, various kinds of measuring instruments, instrument panels for automobiles, word processors, electronic note-books, printers, computers, and televisions. While the liquid crystal display devices employ optical anisotropy and dielectric anisotropy of liquid crystalline compounds, dynamic scattering (DS) mode, guest-host (GH) mode, twisted nematic (TN) mode, super twisted nematic (STN) mode, electrically controlled birefringence (ECB) mode, ferroelectric liquid crystal (FLC) mode are known as their display mode.

While driving mode of the display devices include static driving mode, time division driving mode, active matrix driving mode, and dual frequency driving mode, thin film transistor (TFT) mode in the active matrix drive mode has attracted most public attention from the viewpoint of having a most excellent display performance.

While the properties to be possessed by liquid crystalline compounds to be used for these liquid crystal display devices vary depending on their application, any liquid crystalline compound is required to be stable against environmental factors such as moisture, air, heat, and light, and to exhibit a liquid crystal phase at a range of temperature as wide as possible with room temperature being centered.

In order to develop most suitable characteristics required to each display device, liquid crystal compositions are used in which several kinds, sometimes more than 20 kinds of liquid crystalline compounds are mixed. Accordingly, miscibility with other liquid crystalline compounds is required for liquid crystalline compound. Particularly, the miscibility at low temperatures is recently required for the liquid crystal compound from the necessity of being used under wide variety of environmental conditions.

As the characteristics generally required of the materials mentioned:

1) Material has a wide temperature range of liquid crystal phase. Alternatively, it does not cause a reduction in nematic mesomorphic range when added to a liquid crystal composition.
2) Material has a low viscosity.
3) Material has a large positive value of dielectric anisotropy.
4) Material has a high specific resistance.

In the characteristics mentioned above, "wide temperature range of liquid crystal phase" means that the upper limit temperature of nematic phase is high, that melting point is low, and that phase separation such as separation of crystals scarcely occur even in a range of low temperatures.

Viscosity of the material is an extremely important factor which controls the response speed of liquid crystal molecule to electric field (Phys. Lett., 39A, 69 (1972)), and a liquid crystal composition having a quick response speed (that is, a low viscosity) is most earnestly sought at present.

Driving voltage, particularly the voltage of threshold value (Vth) is a function of the value of dielectric anisotropy as shown by the following equation:

$$Vth = k(K/\Delta\epsilon)^{1/2}$$

wherein k represents a proportional constant, K represents an elastic constant, and $\Delta\epsilon$ represents a value of dielectric anisotropy.

In order to reduce energy consumption, a compound having a large, positive value of dielectric anisotropy is necessary. Exploration for compounds having a large, positive value of dielectric anisotropy is enthusiastically being carried out, and as the compound having a large value of dielectric anisotropy, for example, trifluorophenyl derivatives (10) and trifluoromethoxyphenyl derivatives (11) are known.

Extremely high specific resistance (high VHR: high voltage holding ratio) is required for active matrix liquid crystal displays which are driven with integrated nonlinear devices for switching each segment, particularly for liquid crystal compositions designed for TFT. The reason is that when liquid crystalline compounds or liquid crystal compositions having a low specific resistance is used, electric resistance in a liquid crystal panel is decreased and voltage holding ratio between electrodes is decreased, thus, a problem of decrease of picture contrast, "image sticking" is raised. High specific resistance of liquid crystal composition is an extremely important factor, particularly to warrant utilization life of liquid crystal display devices which are driven at a low voltage.

In Japanese Patent Application Laid-open No. 4-501864, compounds having a branched alkyl group at its side chain are disclosed as liquid crystalline compounds for TFT.

However, no specific description is contained in the Japanese Patent Application Laid-open No. 4-501864 about the values of physical properties of these compounds, and thus the invention disclosed in this publication can not be considered to have been completed. Also, specific compounds which are disclosed in the description in Japanese Patent Application Laid-open No. 4-501864 in connection with composition are only ones containing 3,4,5-trifluorophenyl terminal group.

SUMMARY OF THE INVENTION

An object of the present invention is to provide a novel liquid crystalline compound having a lower viscosity, large, positive value of dielectric anisotropy, high chemical stability, high miscibility with other liquid crystalline compounds at low temperatures, and high specific resistance (high VHR: high voltage holding ratio) at the same time; to provide a liquid crystal composition having the novel liquid crystalline compound and having suitable physical properties; and to provide a liquid crystal display device having the liquid crystal composition.

As a result of the research by the present inventors, compounds have now been found which have improved characteristics compared to known liquid crystalline compounds and have a novel structure, that is, a branched alkyl group at their side chain, to achieve the present invention. That is, the first aspect of the present invention is concerned with a liquid crystalline compound expressed by the following general formula (1)

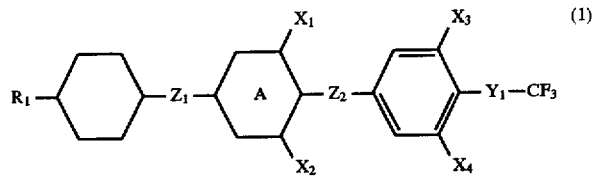

wherein $R_1$ represents a branched alkyl group having 3 to 10 carbon atoms, ring A represents 1,4-phenylene group or 1,4-cyclohexylene group, $Z_1$ and $Z_2$ independently represent a single bond or 1,2-ethylene group, respectively, $X_1$, $X_2$, $X_3$, and $X_4$ independently represent fluorine atom or hydrogen atom, respectively, and $Y_1$ represents oxygen atom or a single bond.

Second aspect of the present invention is concerned with the liquid crystalline compound expressed by the general formula (1) mentioned above wherein $R_1$ is 4-methylpentyl group.

Third aspect of the present invention is concerned with the liquid crystalline compound expressed by the general formula (1) mentioned above wherein $R_1$ is 3-methylpentyl group.

Fourth aspect of the present invention is concerned with the liquid crystalline compound expressed by the general formula (1) mentioned above wherein $R_1$ is 3-methylbutyl group.

Fifth aspect of the present invention is concerned with the liquid crystalline compound expressed by the general formula (1) mentioned above wherein $R_1$ is 2-methylpropyl group.

Sixth aspect of the present invention is concerned with the liquid crystalline compound expressed by the general formula (1) mentioned above wherein $R_1$ is 5-methylhexyl group.

Seventh aspect of the present invention is concerned with a liquid crystal composition comprising at least two components and containing at least one liquid crystalline compound expressed by the general formula (1).

Eighth aspect of the present invention is concerned with a liquid crystal composition containing, as the first component, at least one compound expressed by the general formula (1) and containing, as the second component, at least one compound selected from the group consisting of the compounds expressed by the general formula (2), (3), or (4)

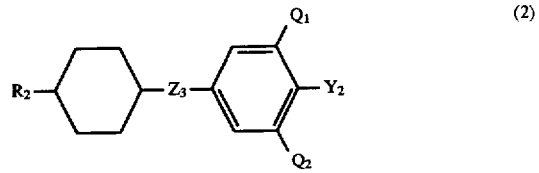

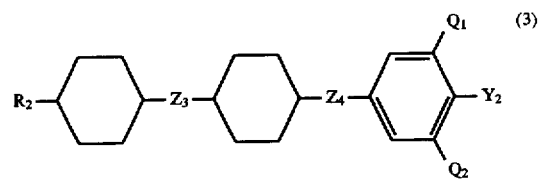

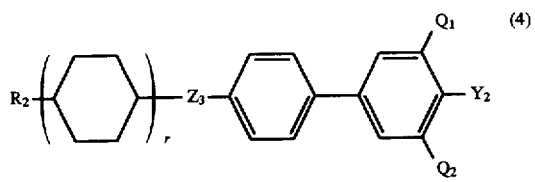

wherein $R_2$ represents an alkyl group having 1 to 10 carbon atoms, $Y_2$ represents fluorine atom or chlorine atom, $Q_1$ and $Q_2$ independently represent fluorine atom or hydrogen atom, respectively, r represents 1 or 2, and $Z_3$ and $Z_4$ independently represent —$CH_2CH_2$— or a single bond.

Ninth aspect of the present invention is concerned with a liquid crystal composition containing, as the first component, at least one compound expressed by the general formula (1) and containing, as the second component, at least one compound selected from the group consisting of the compounds expressed by the general formula (5), (6), (7), (8), or (9)

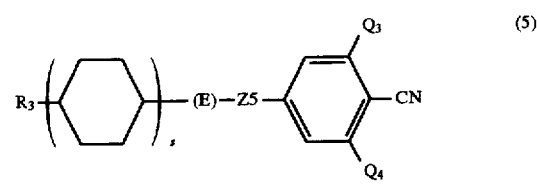

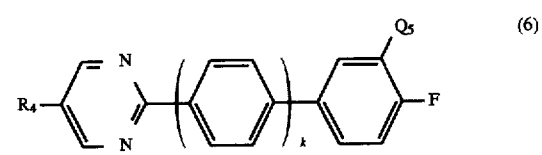

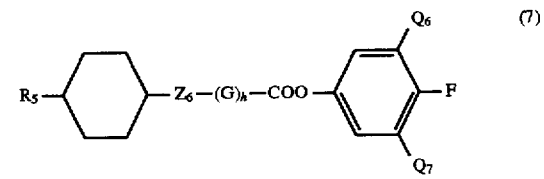

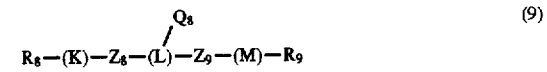

wherein $R_3$ represents an alkyl group having 1 to 10 carbon atoms or an alkenyl group having 2 to 10 carbon atoms, in either case, any methylene group (—$CH_2$—) may be replaced by oxygen atom (—O—), but in neither case, two or more consecutive carbon atoms replaced by oxygen atoms, $Z_5$ represents —$CH_2CH_2$—, —COO—, or a single bond, $Q_3$ and $Q_4$ independently represent fluorine atom or hydrogen atom, (E) represents cyclohexane ring, benzene ring, or 1,3-dioxane ring, and s represents 0 or 1, $R_4$ represents an alkyl group having 1 to 10 carbon atoms, Q5 represents fluorine atom or hydrogen atom, and k represents 0 or 1.

$R_5$ represents an alkyl group having 1 to 10 carbon atoms, (G) represents cyclohexane ring or benzene ring, $Q_6$ and $Q_7$ independently represent fluorine atom or hydrogen atom, $Z_6$ represents —COO— or a single bond, and h represents 0 or 1, $R_6$ and $R_7$ independently represent an alkyl group, alkyloxy group, or alkyloxymethyl group each having 1 to 10 carbon atoms, (H) represents cyclohexane ring, pyrimidine ring, or benzene ring, (J) represents cyclohexane ring or benzene ring, $Z_7$ represents —C≡C—, —COO—, —CH$_2$CH$_2$—, or a single boned, $R_8$ represents an alkyl group or alkoxyl group each having 1 to 10 carbon atoms, $R_9$ represents an alkyl group, alkyloxy group, or alkoxymethyl group each having 1 to 10 carbon atoms, (K) represents cyclohexane ring or pyrimidine ring, (L) and (M) independently represent cyclohexane ring or benzene ring, $Z_8$ represents —COO—, —CH$_2$CH$_2$—, or a single bond, $Z_9$ represents —C≡C—, —COO—, or a single boned, and $Q_8$ represents fluorine atom or hydrogen atom.

Tenth aspect of the present invention is concerned with a liquid crystal display device which uses a liquid crystal composition comprising at least two components and containing at least one compound expressed by the general formula (1).

Eleventh aspect of the present invention is concerned with a liquid crystal display device which uses a liquid crystal composition recited in any one of (7) to (10) of the present invention.

DESCRIPTION OF THE PREFERRED EMBODIMENTS

While the compounds of the present invention expressed by the general formula (1) are characterized by having a branched alkyl group at their side chain, they include specifically the 5 compounds expressed by the following general formulas (1-1) through (1-12)

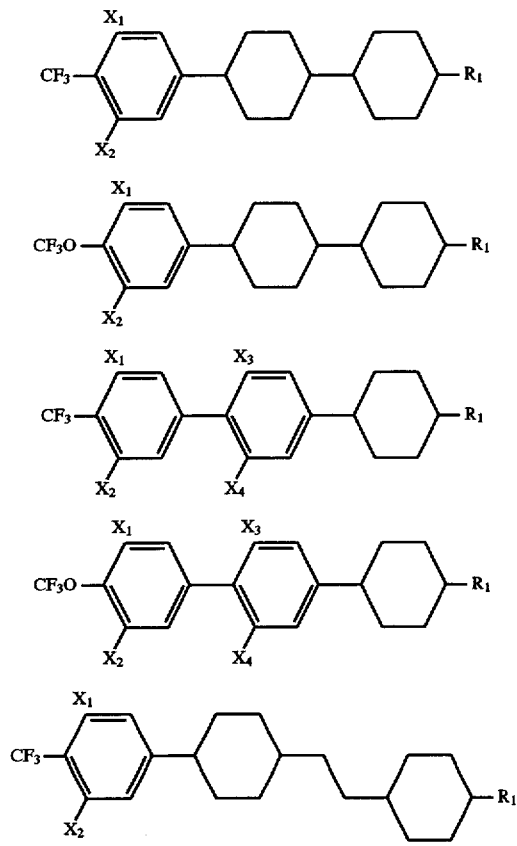
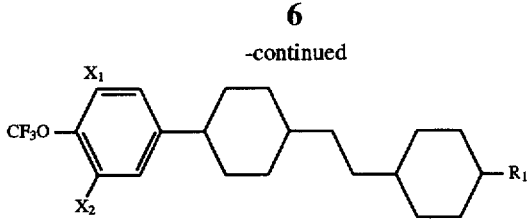
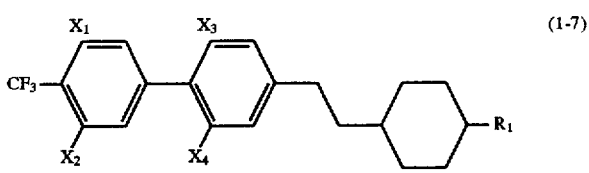
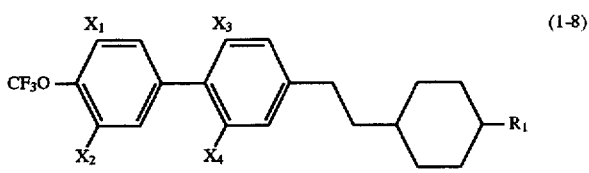
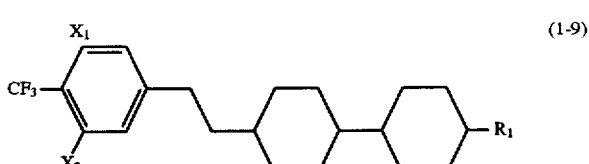
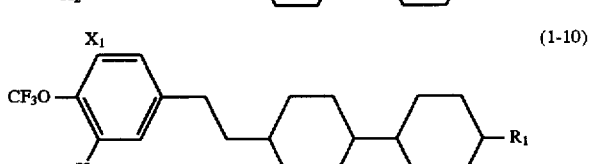
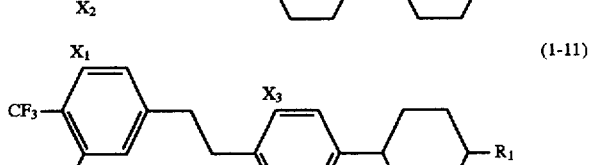
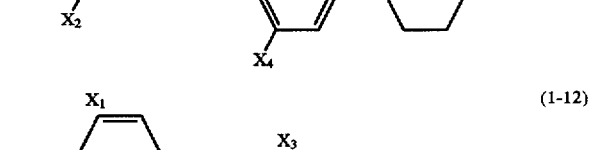

wherein $R_1$, $X_1$, $X_2$, $X_3$, and $X_4$ represent the same meaning as those mentioned above.

Compounds of the present invention expressed by the general formula (1) have a low viscosity, large positive value of dielectric anisotropy, high chemical stability, high miscibility with other liquid crystalline compounds even at low temperatures, and extremely high specific resistance (high VHR: high voltage holding ratio) and good stability against ultra violet light. By using the compounds which are defined by suitably selecting $R_1$, ring A, $Z_1$, $Z_2$, $Y_1$, $X_1$, $X_2$, $X_3$, and $X_4$ in the general formula (1), liquid crystal compositions suitable for their purpose can be prepared. For instance, when a large positive value of dielectric anisotropy is required, the purpose can be achieved by introducing fluorine atom as substituent ($X_1$, $X_2$, $X_3$, and $X_4$) on the ring. When a large value of optical anisotropy is required, it is sufficient to select the compounds in which ring A is 1,4-phenylene group, and when a small value of optical anisotropy is required, it is sufficient to select the compounds in which ring A is 1,4-cyclohexylene group.

Any of the compounds of the present invention expressed by the general formula (1) have a good miscibility with other liquid crystalline compounds or liquid crystal compositions, and the liquid crystal compositions which use the compound do not impair nematic phase even at low temperatures (for instance, at −20° C. which is demanded from practical aspect).

Some of the compounds expressed by the general formula (1), which have a branched alkyl group, exhibit a low viscosity compared to the compounds having a linear alkyl group, depending on the type of branched alkyl group.

Viscosity at 25° C. of the liquid crystal compositions prepared by mixing 85 parts by weight of the composition comprising

| | |
|---|---|
| 4-(4-propylcyclohexyl)benzonitrile | 30% by weight |
| 4-(4-pentylcyclohexyl)benzonitrile | 40% by weight |
| 4-(4-heptylcyclohexyl)benzonitrile | 30% by weight | and 15 parts by weight of a compound expressed by the general formula (1) are shown in Table 1.

TABLE 1

| Compound | | Viscosity (mPa · s) |
|---|---|---|
| 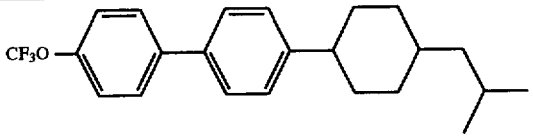 | | 29.2 |
| 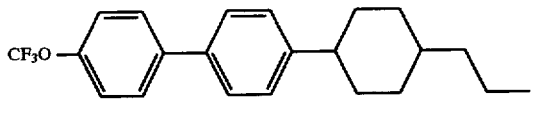 | (Comparative compound) | 24.1 |
| 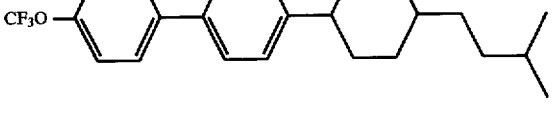 | | 30.2 |
| 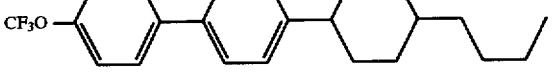 | (Comparative compound) | 29.8 |
| 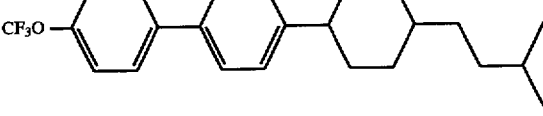 | | 36.0 |
| 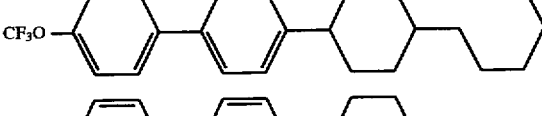 | | 34.8 |
| 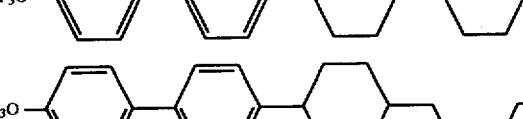 | (Comparative compound) | 39.8 |
| 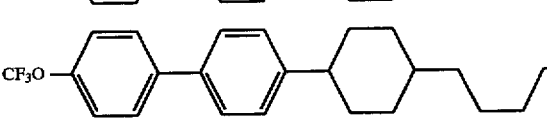 | | 40.0 |
| 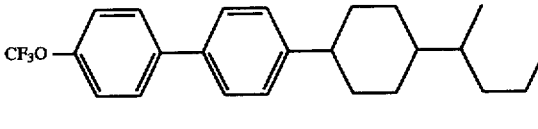 | (Comparative compound) | 39.9 |
|  | | 45.3 |

TABLE 1-continued

| | Viscosity (mPa·s) |
|---|---|
| 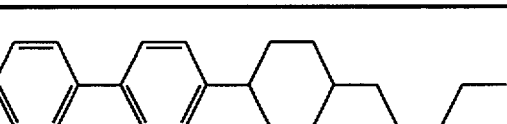 | 39.9 |
| 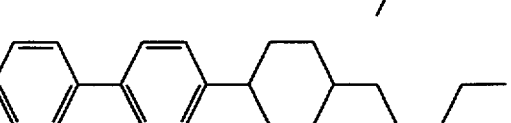 | 36.0 |
| 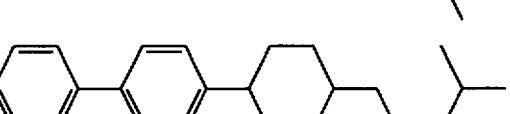 | 34.8 |
| 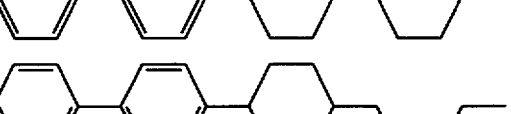 (Comparative compound) | 39.8 |

As will be clear from Table 1, the composition containing a compound having a substituted propyl group or substituted butyl group has a high viscosity compared to, or has the same extent of viscosity as the corresponding composition containing a compound having linear propyl group or linear butyl group. However, the viscosity of the composition in which the compound has a substituted pentyl group is low compared to the corresponding composition in which the compound has a linear pentyl group. Further, when the compound has a hexyl group, this trend is again reversed, and the composition in which the compound has a linear hexyl group has a lower viscosity.

Large correlation exists between the position of methyl branch in a branched alkyl group and viscosity. That is, as shown in Table 1, compositions in which the methyl branch is situated at 1- or 2-position have a higher viscosity compared to corresponding compositions in which the compound has a linear alkyl group, and only the compositions in which the methyl branch is situated at 3- or 4-position have a low viscosity compared to corresponding compositions in which the compound has a linear alkyl group.

Generally, the fact that compounds having a branched alkyl group have a high viscosity compared to those having a linear alkyl group is well known in the art. Thus, it is an extremely surprising fact that the compounds having a lower viscosity can be provided by suitably selecting the position of methyl branch and its chain length as mentioned above.

When the viscosity of liquid crystal compositions is adjusted, a plural number of compounds which have the same basic skeleton but are different only in the chain length of alkyl group are generally mixed to avoid the effects to other physical properties. According to the present invention, when a liquid crystal composition is prepared by using, for instance, 3 kinds of compounds having 3, 4, and 5 chain length of alkyl group (propyl group, butyl group, and pentyl group), respectively, a liquid crystal composition having a lower viscosity can be provided by substituting a compound having a branched pentyl group of the present invention only for the compound having linear pentyl group.

Among the compounds expressed by the general formula (1), typical examples of the compounds particularly having a low viscosity are shown in Tables 2 to 5 with their viscosity, dielectric anisotropy, and optical anisotropy being listed.

TABLE 2

| | Dielectric anisotropy | Optical anisotropy | Viscosity (mPa·s) |
|---|---|---|---|
|  | 6.0 | 0.054 | 53.2 |

TABLE 2-continued

| Structure | Dielectric anisotropy | Optical anisotropy | Viscosity (mPa·s) |
|---|---|---|---|
| CF₃-(3-F-phenyl)-Cy-Cy-CH₂CH(CH₃)C₂H₅ | 9.8 | 0.056 | 64.4 |
| CF₃-(3,5-diF-phenyl)-Cy-Cy-CH₂CH(CH₃)C₂H₅ | 12.4 | 0.054 | 65.2 |
| CF₃-Ph-Ph-Cy-CH₂CH(CH₃)C₂H₅ | 6.7 | 0.124 | 63.2 |
| CF₃-(3-F-phenyl)-Ph-Cy-CH₂CH(CH₃)C₂H₅ | 9.9 | 0.125 | 78.2 |
| CF₃-(3,5-diF-phenyl)-Ph-Cy-CH₂CH(CH₃)C₂H₅ | 12.7 | 0.124 | 82.8 |
| CF₃-Ph-(2-F-phenyl)-Cy-CH₂CH(CH₃)C₂H₅ | 7.6 | 0.123 | 70.2 |
| CF₃-(3-F-phenyl)-(2-F-phenyl)-Cy-CH₂CH(CH₃)C₂H₅ | 10.8 | 0.123 | 89.4 |
| CF₃-(3,5-diF-phenyl)-(2-F-phenyl)-Cy-CH₂CH(CH₃)C₂H₅ | 13.5 | 0.122 | 88.0 |

TABLE 2-continued
| | Dielectric anisotropy | Optical anisotropy | Viscosity (mPa·s) |
|---|---|---|---|
| 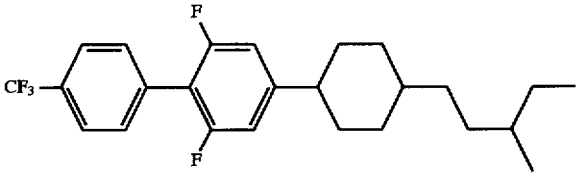 | 7.9 | 0.122 | 68.6 |
| 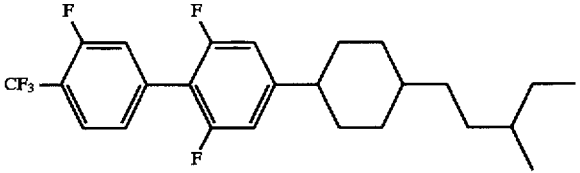 | 11.3 | 0.122 | 83.6 |
| 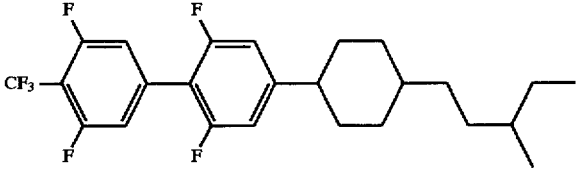 | 14.0 | 0.121 | 88.2 |
TABLE 3
| | Dielectric anisotropy | Optical anisotropy | Viscosity (mPa·s) |
|---|---|---|---|
| 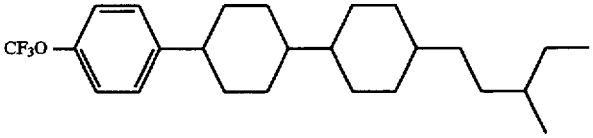 | 8.6 | 0.079 | 27.0 |
| 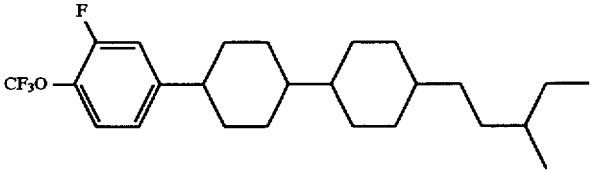 | 10.0 | 0.079 | 36.6 |
| 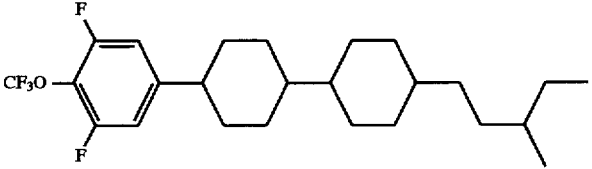 | 9.6 | 0.078 | 33.8 |
| 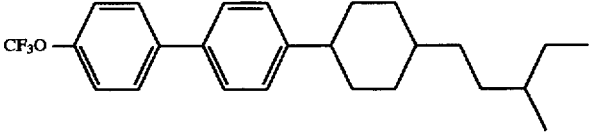 | 10.0 | 0.137 | 36.0 |

TABLE 3-continued

| Structure | Dielectric anisotropy | Optical anisotropy | Viscosity (mPa·s) |
|---|---|---|---|
| CF₃O–[C₆H₃(F)]–[C₆H₄]–[cyclohexyl]–CH₂CH₂CH(CH₃)CH₂CH₃ | 11.0 | 0.138 | 48.6 |
| CF₃O–[C₆H₂(F)(F)]–[C₆H₄]–[cyclohexyl]–CH₂CH₂CH(CH₃)CH₂CH₃ | 9.5 | 0.138 | 50.2 |
| CF₃O–[C₆H₄]–[C₆H₃(F)]–[cyclohexyl]–CH₂CH₂CH(CH₃)CH₂CH₃ | 11.3 | 0.137 | 43.8 |
| CF₃O–[C₆H₃(F)]–[C₆H₃(F)]–[cyclohexyl]–CH₂CH₂CH(CH₃)CH₂CH₃ | 12.5 | 0.137 | 61.2 |
| CF₃O–[C₆H₂(F)(F)]–[C₆H₃(F)]–[cyclohexyl]–CH₂CH₂CH(CH₃)CH₂CH₃ | 11.2 | 0.137 | 58.4 |
| CF₃O–[C₆H₄]–[C₆H₂(F)(F)]–[cyclohexyl]–CH₂CH₂CH(CH₃)CH₂CH₃ | 12.1 | 0.137 | 42.4 |
| CF₃O–[C₆H₃(F)]–[C₆H₂(F)(F)]–[cyclohexyl]–CH₂CH₂CH(CH₃)CH₂CH₃ | 13.6 | 0.137 | 53.6 |
| CF₃O–[C₆H₂(F)(F)]–[C₆H₂(F)(F)]–[cyclohexyl]–CH₂CH₂CH(CH₃)CH₂CH₃ | 12.4 | 0.136 | 59.0 |

TABLE 4

| Structure | Dielectric anisotropy | Optical anisotropy | Viscosity (mPa·s) |
|---|---|---|---|
| CF₃–⌬–⬡–⬡–CH₂CH₂CH(CH₃)₂ | 5.6 | 0.054 | 50.6 |
| 3-F, 4-CF₃ phenyl–⬡–⬡–CH₂CH₂CH(CH₃)₂ | 9.5 | 0.054 | 61.4 |
| 3,5-diF, 4-CF₃ phenyl–⬡–⬡–CH₂CH₂CH(CH₃)₂ | 12.1 | 0.052 | 62.2 |
| CF₃–⌬–⌬–⬡–CH₂CH₂CH(CH₃)₂ | 7.9 | 0.124 | 64.4 |
| 3-F,4-CF₃ phenyl–⌬–⬡–CH₂CH₂CH(CH₃)₂ | 9.5 | 0.123 | 78.8 |
| 3,5-diF,4-CF₃ phenyl–⌬–⬡–CH₂CH₂CH(CH₃)₂ | 12.0 | 0.123 | 84.1 |
| CF₃–⌬–(2-F)⌬–⬡–CH₂CH₂CH(CH₃)₂ | 7.1 | 0.123 | 72.0 |
| 3-F,4-CF₃–(2-F)⌬–⬡–CH₂CH₂CH(CH₃)₂ | 10.6 | 0.122 | 90.8 |
| 3,5-diF,4-CF₃–(2-F)⌬–⬡–CH₂CH₂CH(CH₃)₂ | 13.0 | 0.121 | 89.6 |
| CF₃–⌬–(2,6-diF)⌬–⬡–CH₂CH₂CH(CH₃)₂ | 7.5 | 0.121 | 70.8 |

TABLE 4-continued
| | Dielectric anisotropy | Optical anisotropy | Viscosity (mPa·s) |
|---|---|---|---|
| 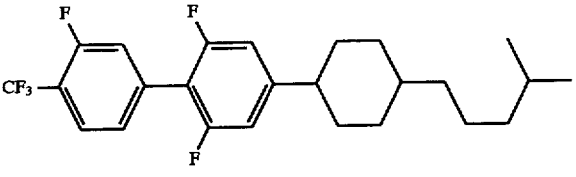 | 11.1 | 0.121 | 83.0 |
| 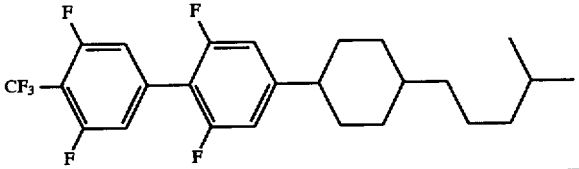 | 13.5 | 0.120 | 90.8 |
TABLE 5
| | Dielectric anisotropy | Optical anisotropy | Viscosity (mPa·s) |
|---|---|---|---|
| 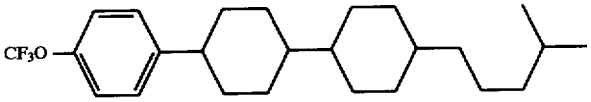 | 8.2 | 0.077 | 26.2 |
| 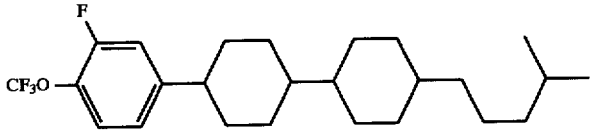 | 9.8 | 0.077 | 36.2 |
| 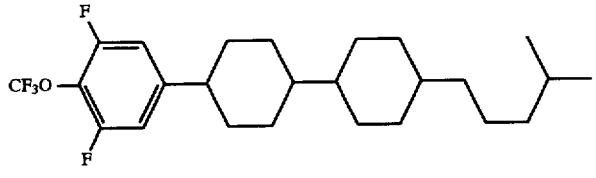 | 9.2 | 0.076 | 34.6 |
| 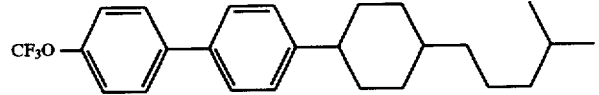 | 9.6 | 0.136 | 34.8 |
| 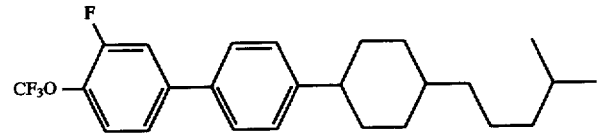 | 10.7 | 0.136 | 49.0 |
| 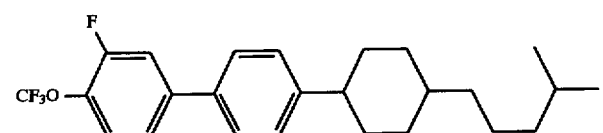 | 9.1 | 0.136 | 50.6 |

TABLE 5-continued

| Structure | Dielectric anisotropy | Optical anisotropy | Viscosity (mPa·s) |
|---|---|---|---|
| CF₃O–[Ph]–[Ph(F)]–[Cy]–CH₂CH(CH₃)– | 12.3 | 0.135 | 42.2 |
| CF₃O–[Ph(F)]–[Ph(F)]–[Cy]–CH₂CH(CH₃)– | 12.1 | 0.135 | 61.8 |
| CF₃O–[Ph(F,F)]–[Ph(F)]–[Cy]–CH₂CH(CH₃)– | 10.8 | 0.135 | 56.6 |
| CF₃O–[Ph]–[Ph(F,F)]–[Cy]–CH₂CH(CH₃)– | 11.7 | 0.136 | 41.0 |
| CF₃O–[Ph(F)]–[Ph(F,F)]–[Cy]–CH₂CH(CH₃)– | 15.2 | 0.135 | 53.6 |
| CF₃O–[Ph(F,F)]–[Ph(F,F)]–[Cy]–CH₂CH(CH₃)– | 12.0 | 0.134 | 57.2 |

It is well known in the art that the compounds having a branched alkyl group have a lower clearing point and are inferior in the properties as liquid crystal compared to those having a linear alkyl group. However, as will be evident from the Tables 2 to 5, among the compounds of the present invention expressed by the general formula (1), the compounds having particularly 3-methylpentyl or 4-methylpentyl group have the same or rather higher clearing point than known compounds having a linear chain.

As mentioned above, whereas the compounds having a branched alkyl group at their side chain are disclosed as liquid crystalline compounds for TFT in Japanese Patent Application Laid-open No. 4-501864, the publication has no specific description about the values of physical properties of the compounds. Thus the facts concerning the relationship between branched alkyl group and viscosity, and the relationship between the branched alkyl group and clearing point as mentioned above can not be expected from the publication.

Liquid crystal composition of the present invention contains at least one compound expressed by the general formula (1) in an amount of 0.1 to 99.9% by weight. The composition is preferably obtained by mixing a second component containing at least one compound selected, depending on the purpose of the liquid crystal composition, from the group consisting of compounds expressed by any one of the general formulas (2) to (9) with a first component containing at least one compound expressed by the general formula (1).

As the compounds which are preferably used in the liquid crystal compositions of the present invention and expressed by any one of the general formulas (2) to (4), the followings can be exemplified:

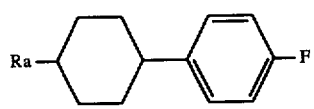 (2-1)
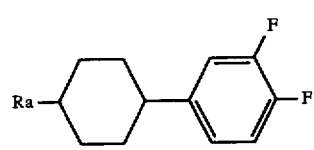 (2-2)
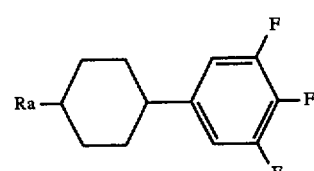 (2-3)
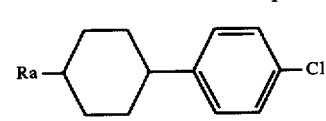 (2-4)
 (2-5)
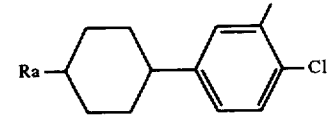 (2-6)
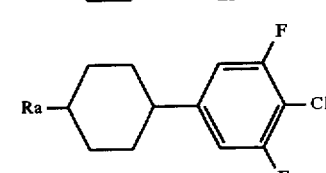 (2-7)
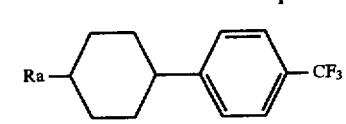 (2-8)
 (2-9)
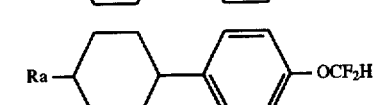 (2-10)
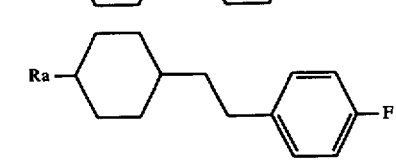 (2-11)
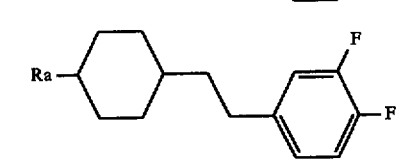 (2-12)

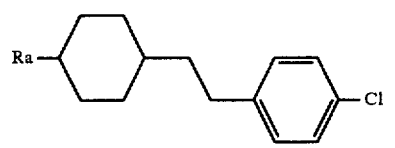 (2-13)
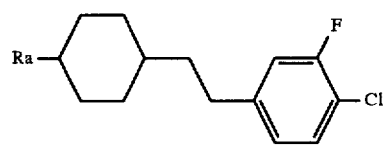 (2-14)
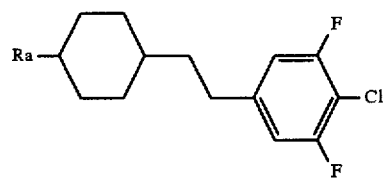 (2-15)
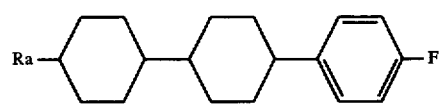 (3-1)
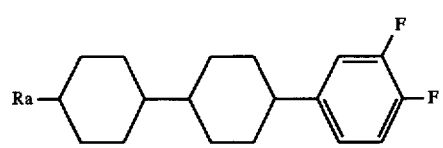 (3-2)
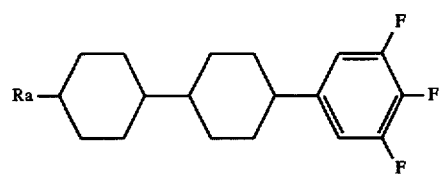 (3-3)
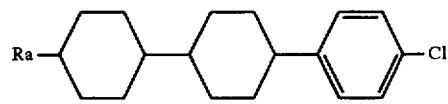 (3-4)
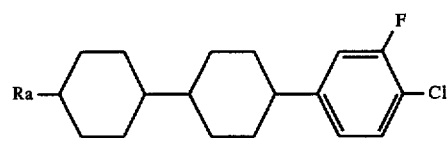 (3-5)
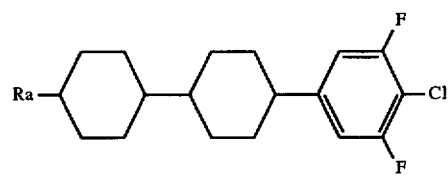 (3-6)
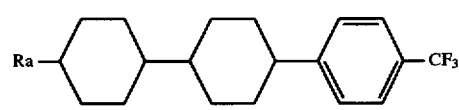 (3-7)
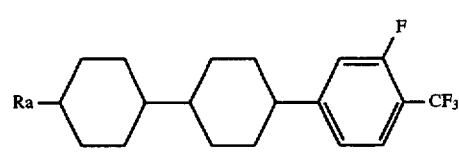 (3-8)

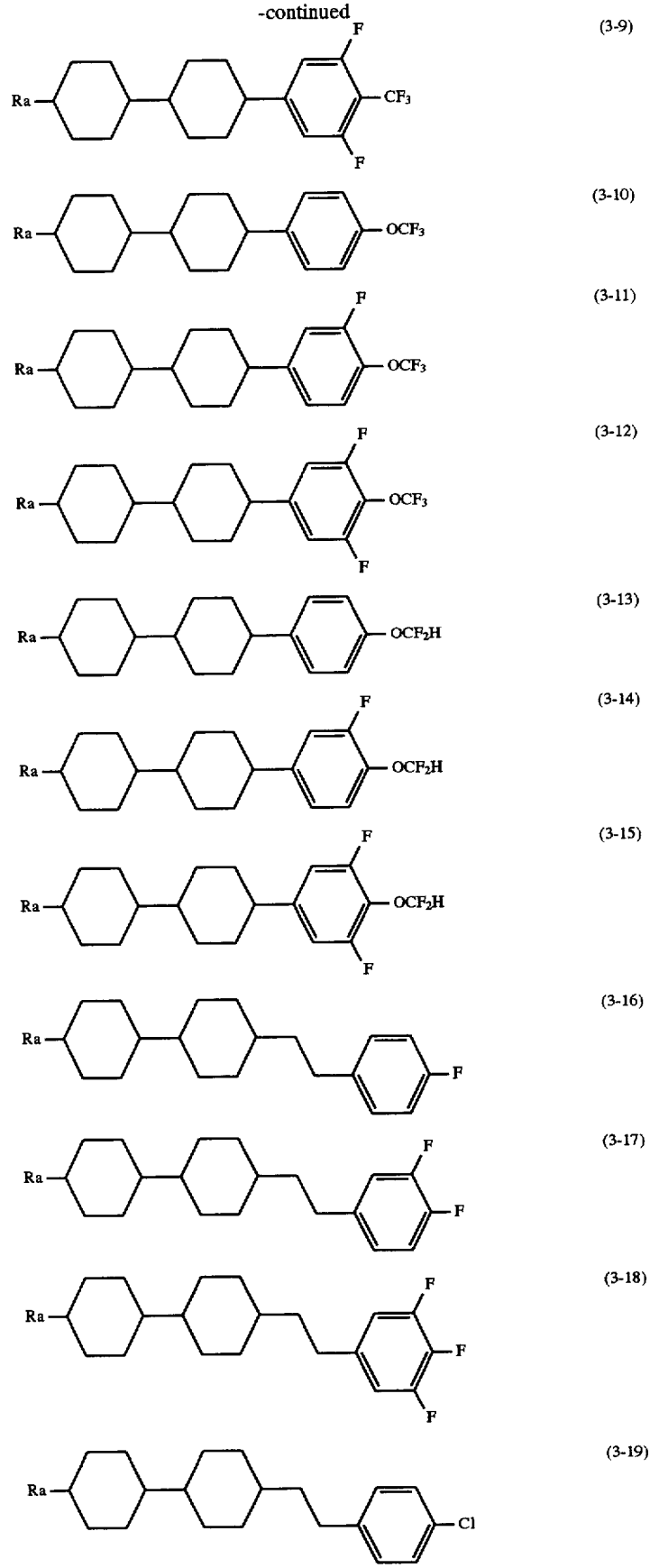

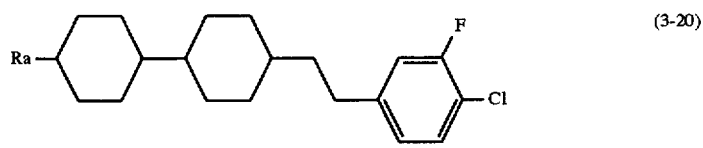 (3-20)
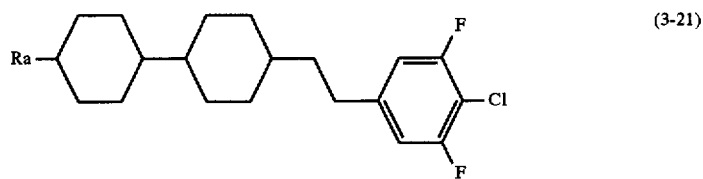 (3-21)
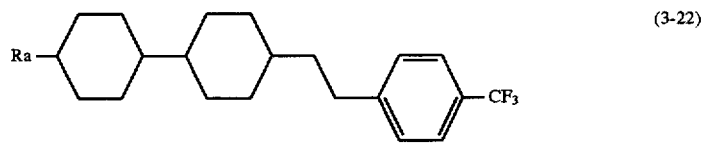 (3-22)
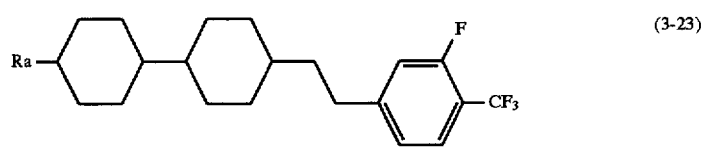 (3-23)
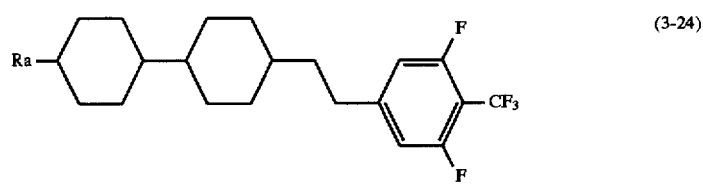 (3-24)
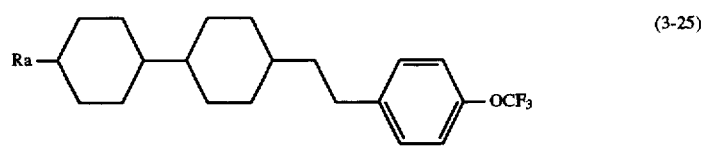 (3-25)
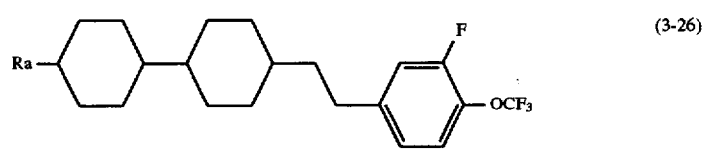 (3-26)
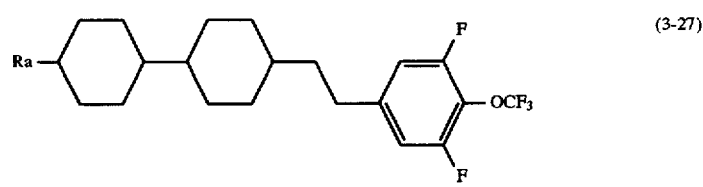 (3-27)
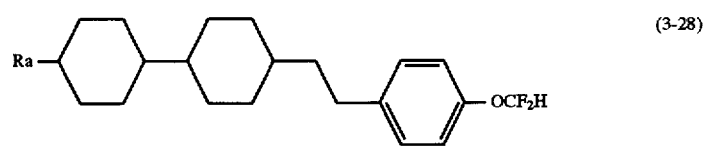 (3-28)
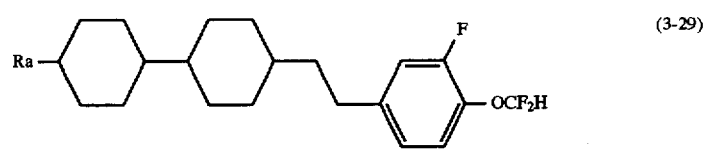 (3-29)

-continued
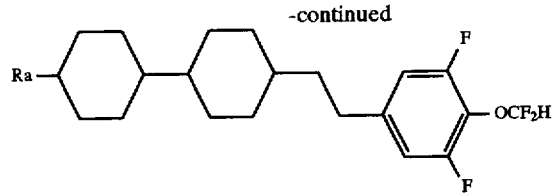 (3-30)
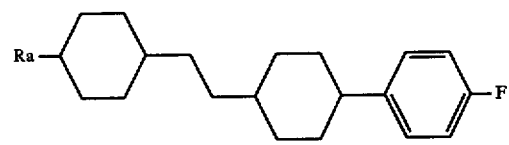 (3-31)
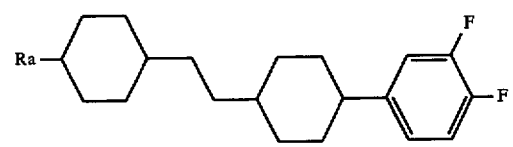 (3-32)
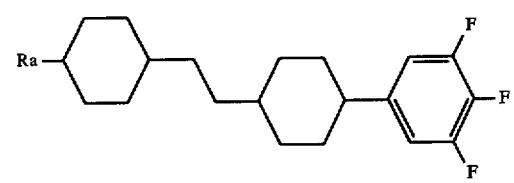 (3-33)
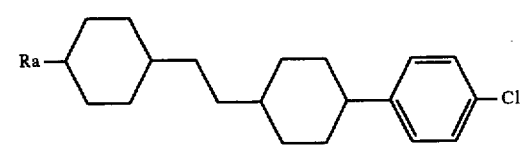 (3-34)
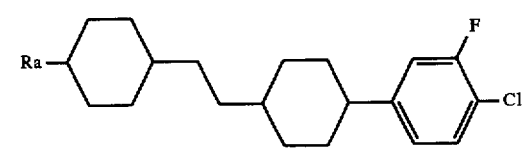 (3-35)
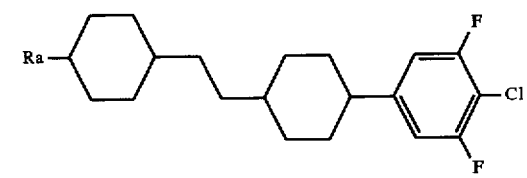 (3-36)
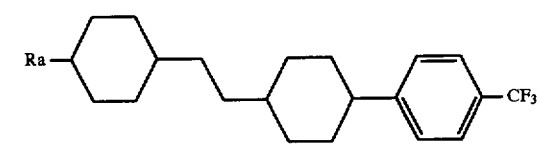 (3-37)
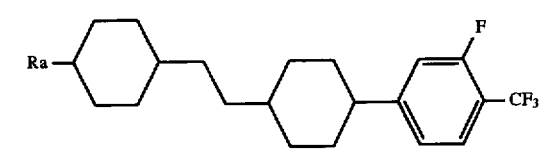 (3-38)
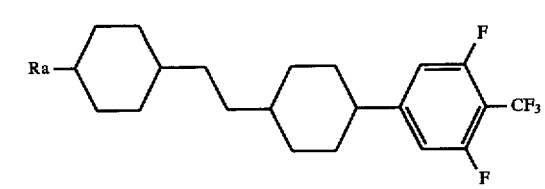 (3-39)

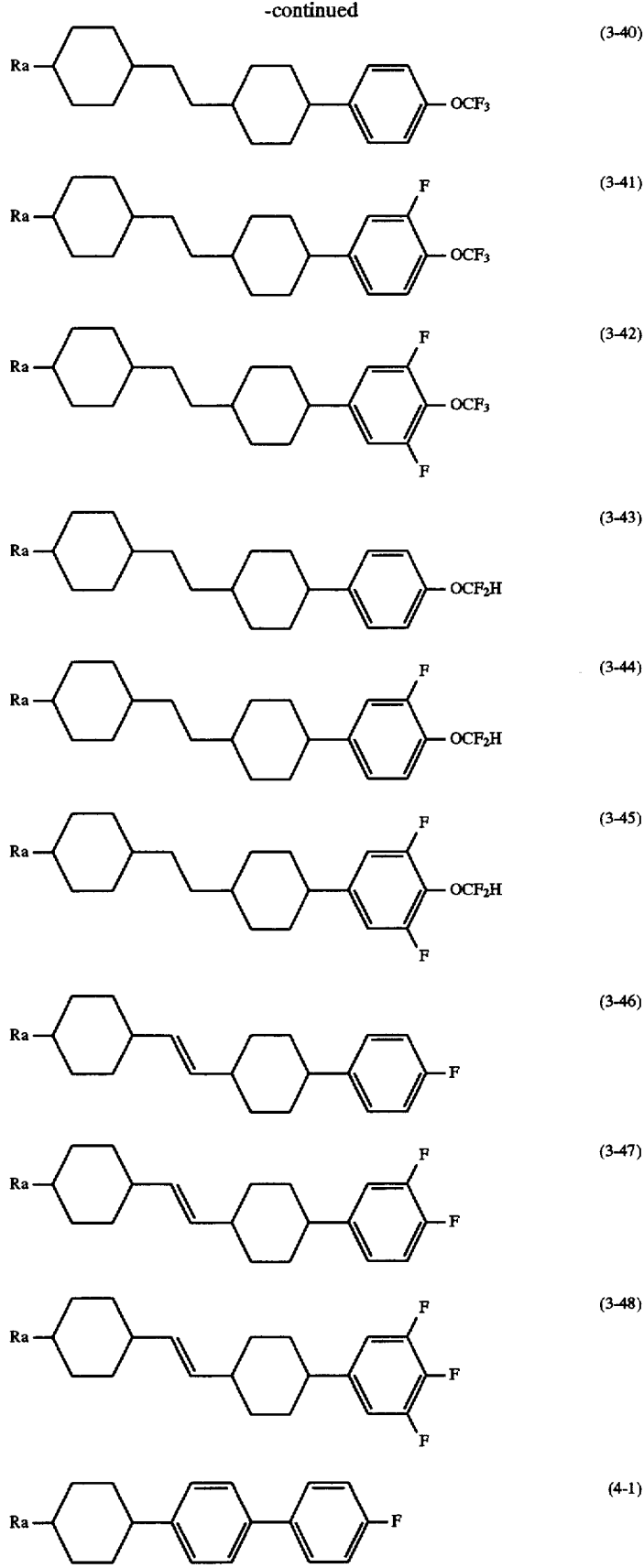

-continued
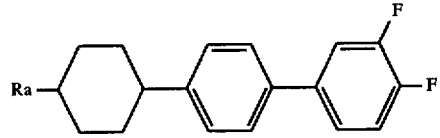 (4-2)
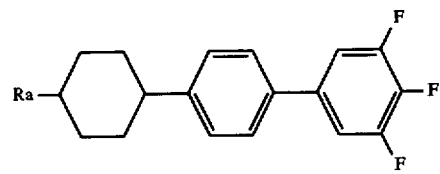 (4-3)
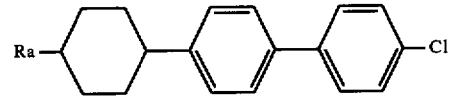 (4-4)
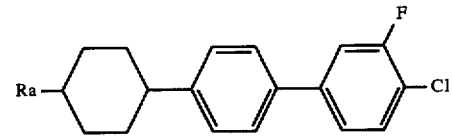 (4-5)
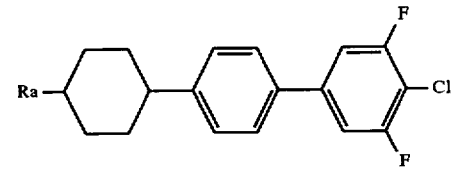 (4-6)
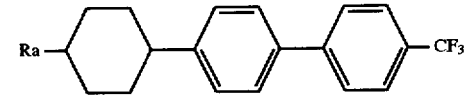 (4-7)
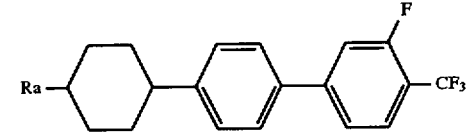 (4-8)
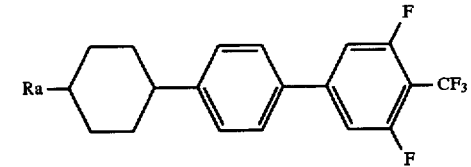 (4-9)
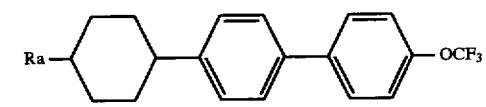 (4-10)
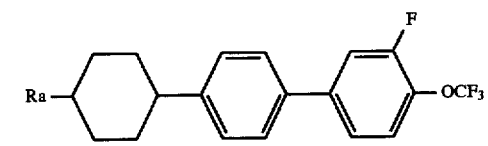 (4-11)
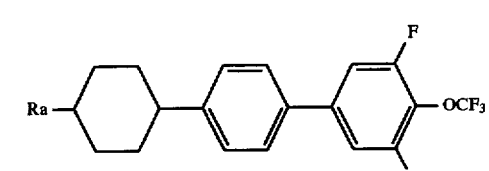 (4-12)

-continued
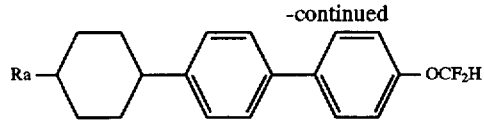 (4-13)
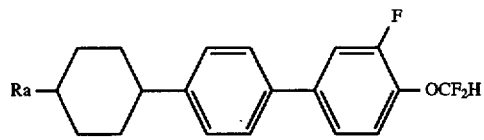 (4-14)
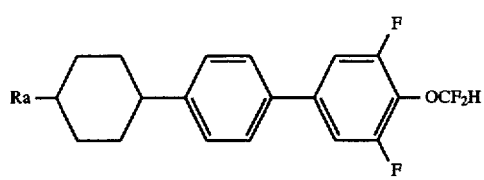 (4-15)
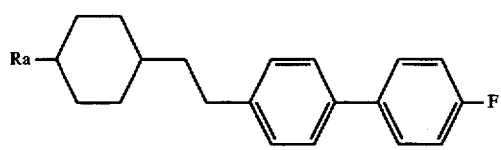 (4-16)
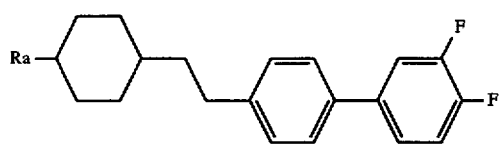 (4-17)
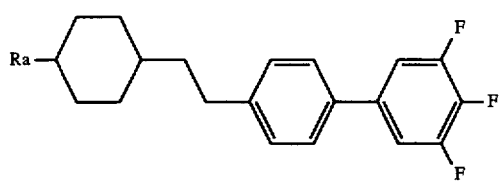 (4-18)
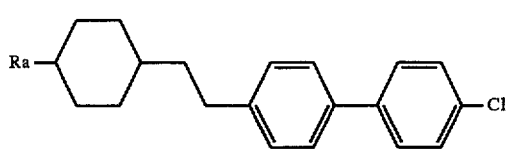 (4-19)
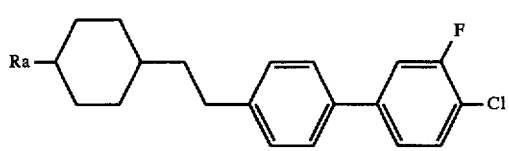 (4-20)
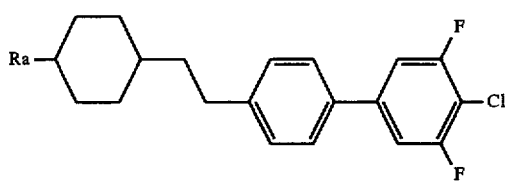 (4-21)
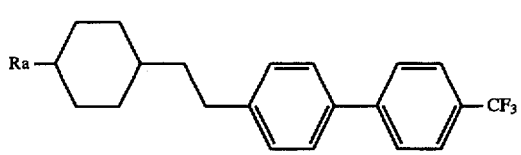 (4-22)

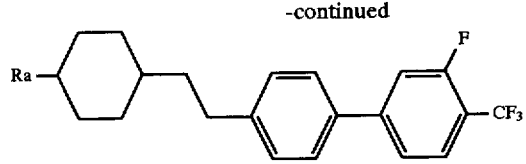 (4-23)
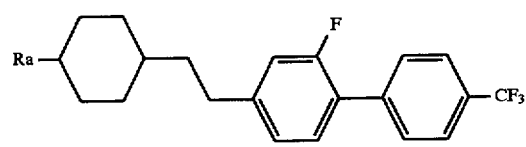 (4-24)
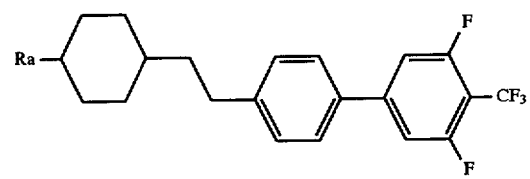 (4-25)
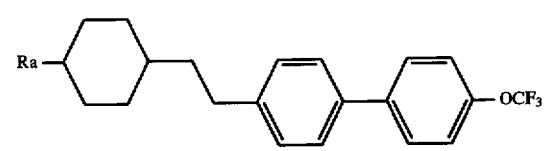 (4-26)
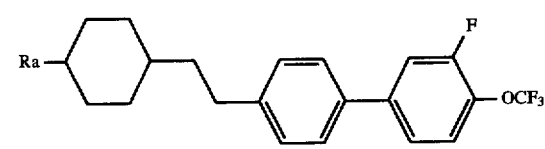 (4-27)
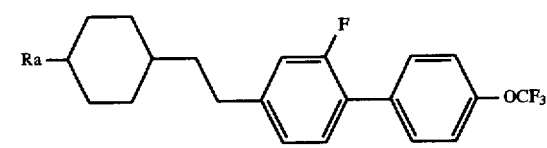 (4-28)
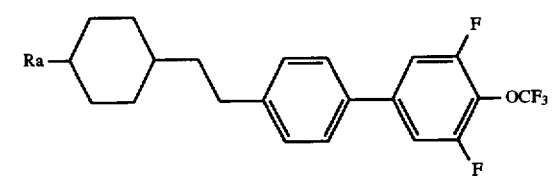 (4-29)
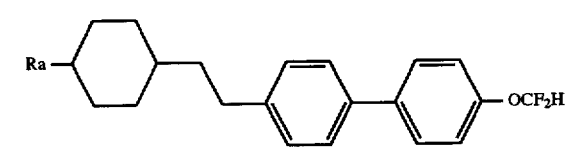 (4-30)
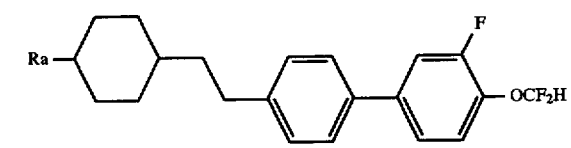 (4-31)
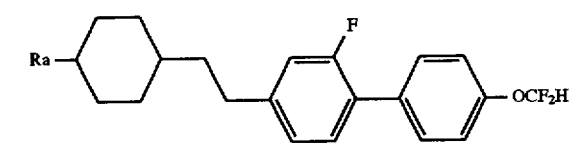 (4-32)

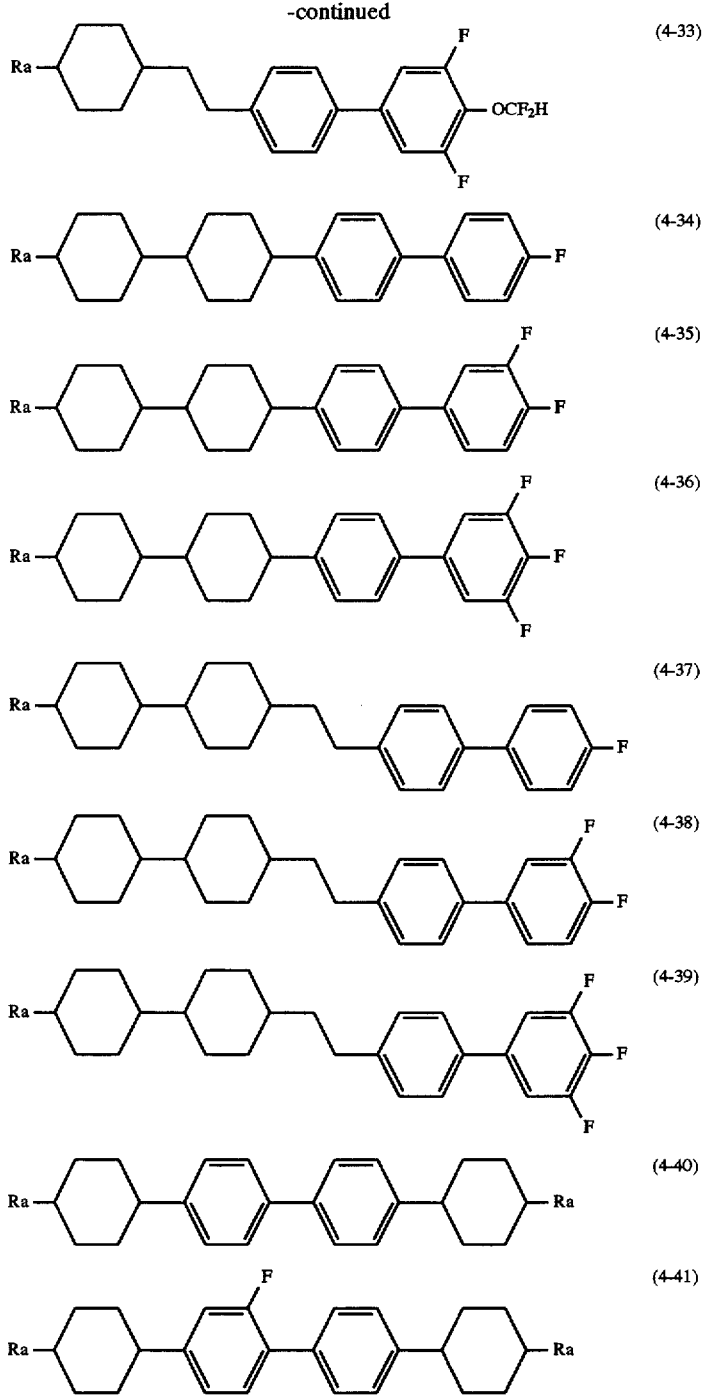

wherein Ra represents an alkyl group or alkoxy group.

Compounds expressed by any one of the general formulas (2) to (4) have a positive value of dielectric anisotropy and are highly excellent in thermal stability and chemical stability. Thus, they are especially useful when liquid crystal compositions for TFT (AM-LCD), for which a high reliability such as a particularly high voltage holding ratio (or high specific resistance) is required, are produced.

When liquid crystal compositions for TFT are produced, while the compounds expressed by any one of the general formulas (2) to (4) can be used in an amount of 1 to 99% by weight based on the total weight of the liquid crystal composition, they are preferably used in a range of 10 to 97% by weight, more desirably in a range of 40 to 95% by weight. In such a liquid crystal composition, compounds expressed by any one of the general formulas (5) to (9) can be included. When the liquid crystal compositions for STN display mode or ordinary TN display mode are produced, the compound expressed by any one of the general formulas (2) to (4) can be used.

As the compounds which are preferably used for the liquid crystal compositions of the present invention and expressed by any one the general formulas (5) to (7), the following can be exemplified:

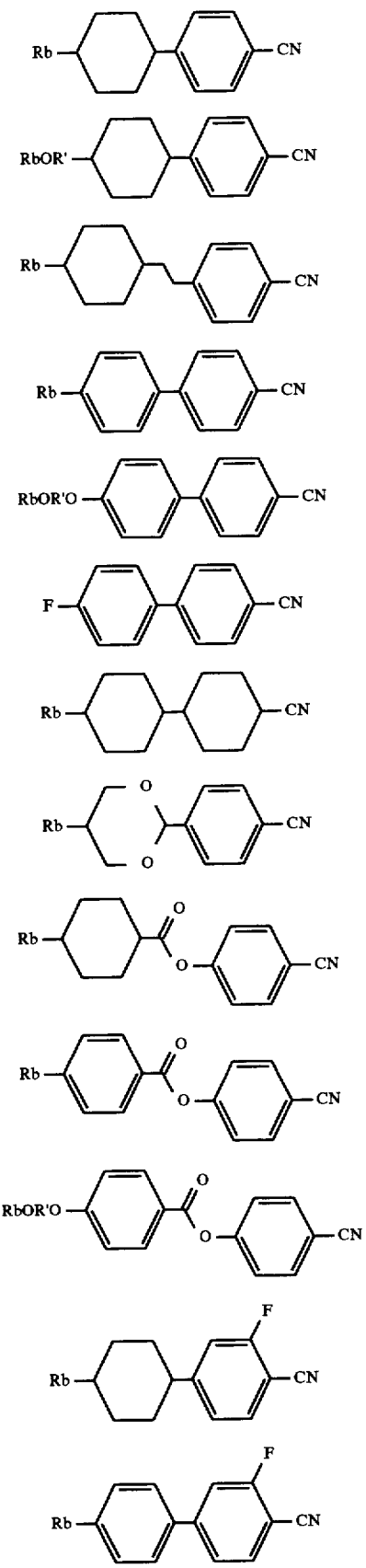
(5-1)
(5-2)
(5-3)
(5-4)
(5-5)
(5-6)
(5-7)
(5-8)
(5-9)
(5-10)
(5-11)
(5-12)
(5-13)
-continued
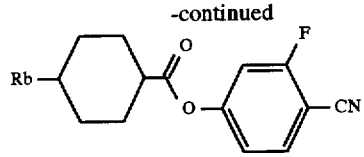 (5-14)
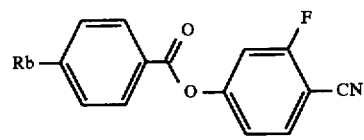 (5-15)
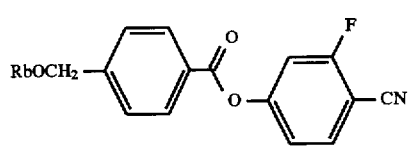 (5-16)
 (5-17)
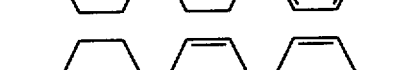 (5-18)
 (5-19)
 (5-20)
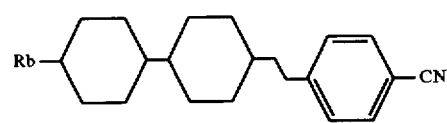 (5-21)
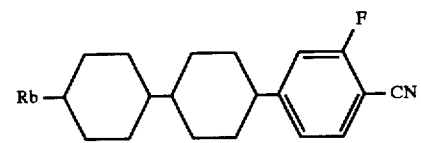 (5-22)
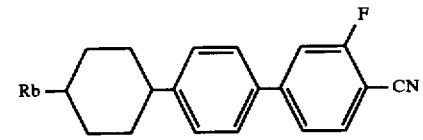 (5-23)
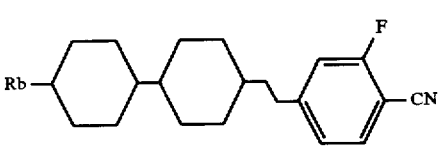 (5-24)
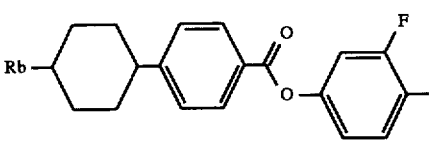 (5-25)
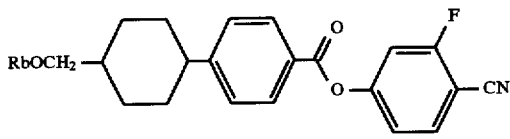

(5-26) (5-27) (6-1) (6-2) (6-3) (7-1) (7-2) (7-3) (7-4) (7-5) (7-6) (7-7) (7-8) (7-9) (7-10) (7-11) (7-12) (7-13)

wherein Rb, Rc, and Rd independently represent an alkyl group or alkenyl group, respectively, and R' represents an α-alkylene group or an ω-alkylene group.

Since the compounds expressed by any one of the general formulas (5) to (7) have a large positive value of dielectric anisotropy, they are useful for reducing the threshold voltage and improving the steepness of electrooptical characteristics of liquid crystal compositions, and they can be used for such purposes as viscosity adjustment, adjustment of the value of optical anisotropy, and raising of clearing point of liquid crystal compositions to widen their nematic range.

As the compounds which are preferably used for the liquid crystal compositions of the present invention and expressed by any one of the general formulas (8) or (9), the following can be exemplified:

(8-1) (8-2)

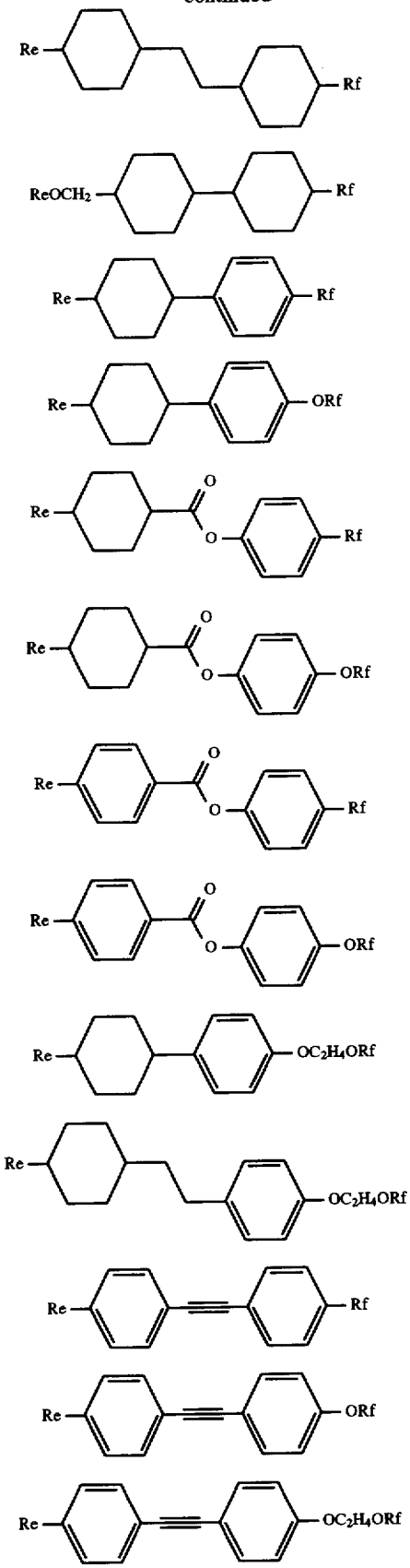
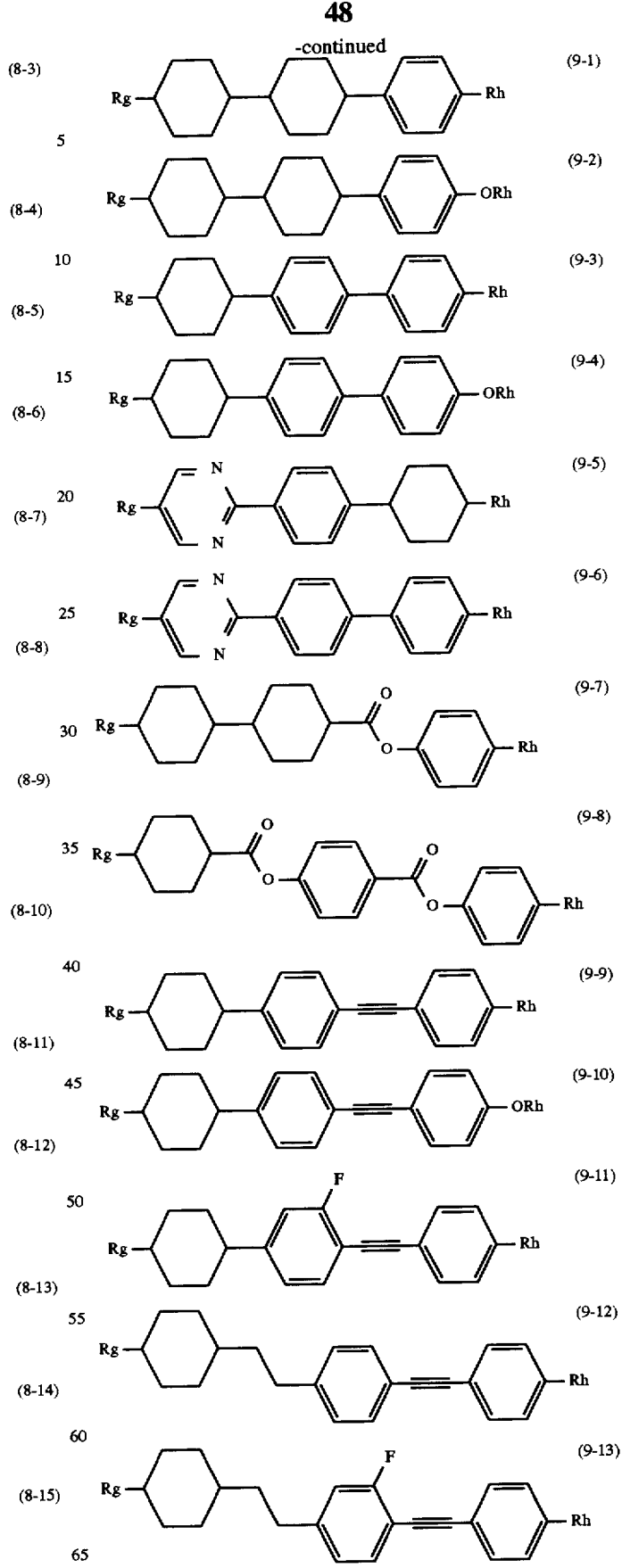

-continued

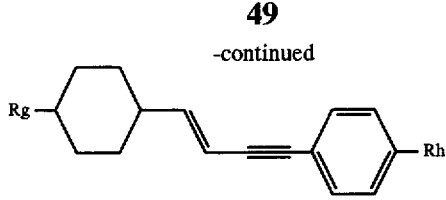

(9-14)

wherein Re, Rf, Rg, and Rh independently represent an alkyl group or alkenyl group, respectively.

The compounds expressed by any one of the general formula (8) or (9) have a negative or slightly positive value of dielectric anisotropy. The compounds expressed by the general formula (8) can be used principally for the purpose of reducing the viscosity and/or adjusting the value of optical anisotropy of liquid crystal compositions. The compounds expressed by the general formula (9) can be used for the purpose of widening nematic range, for instance, by elevating clearing point and/or adjusting the value of optical anisotropy.

As mentioned above, the compounds expressed by any one of the general formulas (5) to (9) are useful when liquid crystal compositions particularly for STN display mode or ordinary TN display mode are produced.

In the liquid crystal compositions of the present invention, while the compounds expressed by any one of the general formulas (5) to (9) can be used in an amount in a range of 1 to 99% by weight, the compounds are preferably used in an amount of 10 to 97% by weight, and more desirably in an amount of 40 to 95% by weight. In the compositions, the compounds expressed by any one of the general formulas (2) to (4) can additionally be included.

By using the liquid crystal compositions of the present invention for TFT liquid crystal display devices, the steepness of electrooptical characteristic and viewing angle can be improved. Further, since the compounds expressed by the general formula (1) have a low viscosity, the liquid crystal display devices which use the compounds can be improved in their response speed.

Liquid crystal compositions of the present invention are prepared by conventional methods, for instance, by the method in which several components are dissolved in each other at a high temperature, or by the method in which each component is mixed by dissolving in an organic solvent, and then the solvent is distilled off under a reduced pressure. Liquid crystal compositions of the present invention can be improved as intended with a suitable additive according to their application, and can be optimized. Such additives are well known in the art and also described in literatures in detail. For instance, a chiral dopant is added to induce the helical structure of liquid crystal adjusting to a required twisting angle, and avoiding reverse-twist.

A dichroic dye such as a merocyanine type, styryl type, azo type, azomethine type, azoxy type, quinophthalone type, anthraquinone type, and tetrazine type dichroic dye can be added to a liquid crystal compositions of the present invention with the object of using as liquid crystal compositions for guest-host mode. Liquid crystal compositions of the present invention Can be used for a polymer dispersion type liquid crystal display devices typified by NCAP which is prepared by forming a nematic liquid crystal into a microcapsule or typified by a polymer network liquid crystal display device (PNLCD) which is prepared by forming a polymer of three-dimensional network structure in a liquid crystal. Also, the liquid crystal compositions of the present invention can be used as liquid crystal compositions for electrically controlled birefringence (ECB) type or dynamic scattering (DS) type.

As the liquid crystal compositions for TFT containing the compounds of the present invention, the following can be exemplified in which "%" means "% by weight":

COMPOSITION EXAMPLE 1

| | |
|---|---|
| 4'-(4-(2-methylpropyl)cyclohexyl)-4-trifluoromethoxybiphenyl (Compound No. 1) | 5% |
| 4'-(4-(3-butylpropyl)cyclohexyl)-4-trifluoromethoxybiphenyl (Compound No. 2) | 5% |
| 4-(4-(4-(4-methylpentyl)cyclohexyl)cyclohexyl)-1-trifluoromethoxybenzene (Compound No. 113) | 11% |
| 5-(4-heptylcylcohexyl)-1,2,3-trifluorobenzene | 5% |
| 4'-(4-propylcylcohexyl)-3,4,5-trifluorobiphenyl | 5% |
| 4'-(4-pentylcylcohexyl)-3,4,5-trifluorobiphenyl | 5% |
| 5-(4-(4-propylcyclohexyl)cyclohexyl)-1,2,3-trifluorobenzene | 7% |
| 5-(4-(4-pentylcyclohexyl)cyclohexyl)-1,2,3-trifluorobenzene | 5% |
| 5-(2-(4-(4-propylcyclohexyl)cyclohexyl)ethyl)-1,2,3-trifluorobenzene | 8% |
| 5-(2-(4-(4-pentylcyclohexyl)cyclohexyl)ethyl)-1,2,3-trifluorobenzene | 5% |
| 5-(4-(2-(4-propylcyclohexyl)ethyl)cyclohexyl)-1,2,3-trifluorobenzene | 7% |
| 5-(4-(2-(4-butylcyclohexyl)ethyl)cyclohexyl)-1,2,3-trifluorobenzene | 7% |
| 5-(4-(2-(4-pentylcyclohexyl)ethyl)cyclohexyl)-1,2,3-trifluorobenzene | 7% |
| 3,4,5-trifluorophenyl-4-(4-propylcyclohexyl)cyclohexanecarboxylate | 8% |
| 3,4,5-trifluorophenyl-4-(4-butylcyclohexyl)cyclohexanecarboxylate | 3% |
| 3,4,5-trifluorophenyl-4-(4-pentylcyclohexyl)cyclohexanecarboxylate | 3% |
| 3,4,5-trifluorophenyl-4-(4-propylcyclohexyl)benzoate | 2% |
| 3,4,5-trifluorophenyl-4-(4-pentylcyclohexyl)benzoate | 2% |

COMPOSITION EXAMPLE 2

| | |
|---|---|
| 4-(4-(4-(4-methylpentyl)cyclohexyl)cyclohexyl)-1-trifluoromethoxybenzene (Compound No. 113) | 8% |
| 4-(4-(4-(4-methylpentyl)cyclohexyl)cyclohexyl)-1-trifluoromethoxy-2-fluorobenzene (Compound No. 114) | 8% |
| 4-(4-(4-(4-methylpentyl)cyclohexyl)cyclohexyl)-1-trifluoromethoxy-2,3-difluorobenzene (Compound No. 115) | 9% |
| 5-(4-heptylcyclohexyl)-1,2,3-trifluorobenzene | 10% |
| 5-(4-(2-(4-propylcyclohexyl)ethyl)cyclohexyl)-1,2,3-trifluorobenzene | 3% |
| 5-(4-(2-(4-butylcyclohexyl)ethyl)cyclohexyl)-1,2,3-trifluorobenzene | 3% |
| 5-(4-(2-(4-pentylcyclohexyl)ethyl)cyclohexyl)-1,2,3-trifluorobenzene | 3% |
| 5-(2-(4-(4-propylcyclohexyl)cyclohexyl)ethyl)-1,2,3-trifluorobenzene | 10% |
| 4'-(4-propylcyclohexyl)-3,4,5-trifluorobiphenyl | 8% |
| 4'-(4-pentylcyclohexyl)-3,4,5-trifluorobiphenyl | 20% |
| 4'-(4-(4-ethylcyclohexyl)cyclohexyl)-3,4,5-trifluorobiphenyl | 4% |
| 4'-(2-(4-propylcyclohexyl)cyclohexyl)ethyl)-3,4,5-trifluorobiphenyl | 5% |
| 4'-(2-(4-(4-butylcyclohexyl)cyclohexyl)ethyl)-3,4,5 trifluorobiphenyl | 6% |
| 4'-(2-(4-(4-pentylcyclohexyl)cyclohexyl)ethyl)-3,4,5-trifluorobiphenyl | 3% |

COMPOSITION EXAMPLE 3

| | |
|---|---|
| 4'-(4-(3-methylpentyl)cyclohexyl)-4-trifluoromethoxybiphenyl (Compound No. 44) | 6% |
| 4'-(4-(4-methylpentyl)cyclohexyl)-4-trifluoromethoxybiphenyl (Compound No. 80) | 6% |
| 4-(4-(4-(4-methylpentyl)cyclohexyl)cyclohexyl)-1-trifluoromethoxy-2-fluorobenzene (Compound No. 114) | 7% |
| 4-(4-(4-(4-methylpentyl)cyclohexyl)cyclohexyl)-1-trifluoromethoxy-2,3-difluorobenzene (Compound No. 115) | 7% |
| 5-(4-heptylcyclohexyl)-1,2,3-trifluorobenzene | 5% |
| 4-(4-(4-ethylcyclohexyl)cyclohexyl)-1,2-difluorobenzene | 10% |
| 4-(4-(4-propylcyclohexyl)cyclohexyl)-1,2-difluorobenzene | 10% |
| 4-(4-(4-pentylcyclohexyl)cyclohexyl)-1,2-difluorobenzene | 10% |

-continued

| | |
|---|---|
| 4-(4-(2-(4-ethylcyclohexyl)ethyl)cyclohexyl)-1,2-difluorobenzene | 4% |
| 4-(4-(2-(4-propylcyclohexyl)ethyl)cyclohexyl)-1,2-difluorobenzene | 2% |
| 4-(4-(2-(4-pentylcyclohexyl)ethyl)cyclohexyl)-1,2-difluorobenzene | 4% |
| 5-(4-(2-(4-propylcyclohexyl)ethyl)cyclohexyl)-3,4,5-trifluorobenzene | 4% |
| 5-(4-(2-(4-butylcyclohexyl)ethyl)cyclohexyl)-3,4,5-trifluorobenzene | 3% |
| 5-(4-(2-(4-pentylcyclohexyl)ethyl)cyclohexyl)-3,4,5-trifluorobenzene | 3% |
| 5-(4-(4-propylcyclohexyl)cyclohexyl)-3,4,5-trifluorobenzene | 6% |
| 5-(4-(4-butylcyclohexyl)cyclohexyl)-3,4,5-trifluorobenzene | 3% |
| 5-(2-(4-propylcyclohexyl)cyclohexyl)ethyl)-3,4,5-trifluorobenzene | 5% |
| 5-(2-(4-(4-pentylcyclohexyl)cyclohexyl)ethyl)-3,4,5-trifluorobenzene | 5% |

COMPOSITION EXAMPLE 4

| | |
|---|---|
| 4'-(4-(5-methylhexyl)cyclohexyl)-4-trifluoromethoxybiphenyl (Compound No. 149) | 10% |
| 4-(4-(4-(4-methylpentyl)cyclohexyl)cyclohexyl)-1-trifluoromethoxy-2-fluorobenzene (Compound No. 114) | 10% |
| 4-(2-(4-pentylcyclohexyl)ethyl)-1,2-difluorobenzene | 4% |
| 4-(4-heptylcyclohexyl)-1,2-difluorobenzene | 8% |
| 4-(4-(4-ethylcyclohexyl)cyclohexyl)-1,2-difluorobenzene | 10% |
| 4-(4-(4-propylcyclohexyl)cyclohexyl)-1,2-difluorobenzene | 10% |
| 4-(4-(4-pentylcyclohexyl)cyclohexyl)-1,2-difluorobenzene | 10% |
| 4-(4-(2-(4-ethylcyclohexyl)ethyl)cyclohexyl)-1,2-difluorobenzene | 10% |
| 4-(4-(2-(4-propylcyclohexyl)ethyl)cyclohexyl)-1,2-difluorobenzene | 5% |
| 4-(4-(2-(4-pentylcyclohexyl)ethyl)cyclohexyl)-1,2-difluorobenzene | 10% |
| 4'-(4-ethylcyclohexyl)-3,4-difluorobiphenyl | 2% |
| 4'-(4-propylcyclohexyl)-3,4-difluorobiphenyl | 2% |
| 4'-(4-pentylcyclohexyl)-3,4-difluorobiphenyl | 4% |
| 4-(4-(4-propylcyclohexyl)cyclohexyl)-1-fluorobenzene | 5% |

COMPOSITION EXAMPLE 5

| | |
|---|---|
| 4'-(4-(3-butylpropyl)cyclohexyl)-4-trifluoromethoxybiphenyl (Compound No. 2) | 5% |
| 4'-(4-(3-methylpentyl)cyclohexyl)-4-trifluoromethoxybiphenyl (Compound No. 44) | 5% |
| 4-(4-(4-(4-methylpentyl)cyclohexyl)cyclohexyl)-1-trifluoromethoxybenzene (Compound No. 113) | 15% |
| 4-(4-heptylcyclohexyl)-1,2-difluorobenzene | 3% |
| 4-fluorophenyl=4-pentylcyclohexanecarboxylate | 6% |
| 4-fluorophenyl=4-heptylcyclohexanecarboxylate | 6% |
| 4-(4-methoxymethylcyclohexyl)-1-pentylcyclohexane | 3% |
| 4-(4-(4-propylcyclohexyl)cyclohexyl)-1-methoxybenzene | 5% |
| 4-(4-(4-propylcyclohexyl)cyclohexyl)-1-fluorobenzene | 5% |
| 4-fluorophenyl=4-(4-propylcyclohexyl)cyclohexanecarboxylate | 4% |
| 4-fluorophenyl=4-(4-pentylcyclohexyl)cyclohexane carboxylate | 4% |
| 4-(4-(4-ethylcyclohexyl)cyclohexyl)-1,2-difluorobenzene | 7% |
| 4-(4-(4-propylcyclohexyl)cyclohexyl)-1,2-difluorobenzene | 7% |
| 4-(4-(4-pentylcyclohexyl)cyclohexyl)-1,2-difluorobenzene | 7% |
| 4'-(4-ethylcyclohexyl)-3,4-difluorobiphenyl | 5% |
| 4'-(4-propylcyclohexyl)-3,4-difluorobiphenyl | 5% |
| 4'-(4-pentylcyclohexyl)-3,4-difluorobiphenyl | 10% |

COMPOSITION EXAMPLE 6

| | |
|---|---|
| 4'-(4-(2-methylpropyl)cyclohexyl)-4-trifluoromethoxybiphenyl (Compound No. 1) | 5% |
| 4'-(4-(4-methylpentyl)cyclohexyl)-4-trifluoromethoxybiphenyl (Compound No. 80) | 5% |
| 4-(4-(4-(4-methylpentyl)cyclohexyl)cyclohexyl)-1-trifluoromethoxy-2-fluorobenzene (Compound No. 114) | 20% |
| 4-(4-(4-ethylcyclohexyl)cyclohexyl)-1,2-difluorobenzene | 12% |
| 4-(4-(4-propylcyclohexyl)cyclohexyl)-1,2-difluorobenzene | 12% |
| 4-(4-(4-pentylcyclohexyl)cyclohexyl)-1,2-difluorobenzene | 12% |
| 4-(4-propylcyclohexyl)-1-ethoxybenzene | 10% |
| 4-(4-(4-propylcyclohexyl)cyclohexyl)-1-methylbenzene | 5% |
| 4-(4-(4-propylcyclohexyl)cyclohexyl)-1-propylbenzene | 5% |
| 4'-(4-ethylcyclohexyl)-4-fluorobiphenyl | 4% |
| 4'-(4-propylcyclohexyl)-4-fluorobiphenyl | 4% |
| 4-fluorophenyl-4-(4-propylcyclohexyl)cyclohexanecarboxylate | 3% |
| 4-fluorophenyl-4-(4-pentylcyclohexyl)cyclohexanecarboxylate | 3% |
| 4-fluorophenyl-4-(4-propylcyclohexyl)benzoate | 3% |

COMPOSITION EXAMPLE 7

| | |
|---|---|
| 4'-(4-2-methylpropyl)cyclohexyl)-4-trifluoromethoxybiphenyl (Compound No. 1) | 13% |
| 4'-(4-ethylcyclohexyl)-3,4-difluorobiphenyl | 3% |
| 4'-(4-propylcyclohexyl)-3,4-difluorobiphenyl | 3% |
| 4'-(4-pentylcyclohexyl)-3,4-difluorobiphenyl | 6% |
| 4'-(4-ethylcyclohexyl)-4-fluorobiphenyl | 3% |
| 4'-(4-propylcyclohexyl)-4-fluorobiphenyl | 3% |
| 5-(4-(2-(4-propylcyclohexyl)ethyl)cyclohexyl)-1,2,3-trifluorobenzene | 7% |
| 5-(4-(2-(4-butylcyclohexyl)ethyl)cyclohexyl)-1,2,3-trifluorobenzene | 7% |
| 5-(4-(2-(4-pentylcyclohexyl)ethyl)cyclohexyl)-1,2,3-trifluorobenzene | 7% |
| 5-(4-(4-propylcyclohexyl)cyclohexyl)-1,2,3-trifluorobenzene | 3% |
| 5-(4-(4-butylcyclohexyl)cyclohexyl)-1,2,3-trifluorobenzene | 3% |
| 5-(2-(4-(4-propylcyclohexyl)cyclohexyl)ethyl)-1,2,3-trifluorobenzene | 10% |
| 5-(2-(4-(4-pentylcyclohexyl)cyclohexyl)ethyl)-1,2,3-trifluorobenzene | 8% |
| 4'-(4-propylcyclohexyl)-3,4,5-trifluorobiphenyl | 8% |
| 4'-(4-pentylcyclohexyl)-3,4,5-trifluorobiphenyl | 8% |
| 4-(4-(4-propylcyclohexyl)cyclohexyl)-1-chlorobenzene | 4% |
| 4-(4-(4-pentylcyclohexyl)cyclohexyl)-1-chlorobenzene | 4% |

COMPOSITION EXAMPLE 8

| | |
|---|---|
| 4'-(4-(5-methylhexyl)cyclohexyl)-4-trifluoromethoxybiphenyl (Compound No. 149) | 8% |
| 4-(4-(4-(4-methylpentyl)cyclohexyl)cyclohexyl)-1-trifluoromethoxy-2,3-difluorobenzene (Compound No. 115) | 10% |
| 5-(4-heptylcyclohexyl)-1,2,3-trifluorobenzene | 5% |
| 4-(4-propylcyclohexyl)-1-chlorobenzene | 7% |
| 4-(2-(4-ethylphenyl)ethynyl)-4-methoxybenzene | 8% |
| 4'-(4-ethylcyclohexyl)-3,4-difluorobiphenyl | 2% |
| 4'-(4-propylcyclohexyl)-3,4-difluorobiphenyl | 2% |
| 4'-(4-pentylcyclohexyl)-3,4,5-trifluorobiphenyl | 4% |
| 4'-(4-propylcyclohexyl)-3,4,5-trifluorobiphenyl | 6% |
| 4'-(4-pentylcyclohexyl)-3,4-difluorobiphenyl | 6% |
| 4-(4-(4-ethylcyclohexyl)cyclohexyl)-1-chlorobenzene | 5% |
| 4-(4-(4-propylcyclohexyl)cyclohexyl)-1-chlorobenzene | 5% |
| 4-(2-(2-fluoro-4-(4-propylcyclohexyl)phenyl)ethynyl)-1-ethylbenzene | 5% |
| 4-(2-(2-fluoro-4-(4-propylcyclohexyl)phenyl)ethynyl)-1-propylbenzene | 5% |
| 4-(2-(2-fluoro-4-(4-propylcyclohexyl)phenyl)ethynyl)-1-butylbenzene | 5% |
| 4-(2-(4-(2-(4-propylcyclohexyl)ethyl)phenyl)ethynyl)-1-ethylbenzene | 4% |
| 4-(2-(4-(2-(4-propylcyclohexyl)ethyl)phenyl)ethynyl)-1-propylbenzene | 4% |

-continued

| | |
|---|---|
| 4-(2-(2-fluoro-4-(4-propylcyclohexyl)phenyl)ethenyl)-1-ethylbenzene | 3% |
| 4-(4-(2-(4-propylcyclohexyl)ethyl)cyclohexyl)-1-chloro-2-fluorobenzene | 3% |
| 4-(4-(2-(4-pentylcyclohexyl)ethyl)cyclohexyl)-1-chloro-2-fluorobenzene | 3 |

COMPOSITION EXAMPLE 9

| | |
|---|---|
| 4-(4-(4-(4-methylpentyl)cyclohexyl)cyclohexyl)-1-trifluoromethoxybenzene (Compound No. 113) | 9% |
| 4-(4-(4-(4-methylpentyl)cyclohexyl)cyclohexyl)-1-trifluoromethoxy-2-fluorobenzene (Compound No. 114) | 9% |
| 4-(4-propylcyclohexyl)benzonitrile | 12% |
| 4-(4-propylcyclohexyl)-1-ethoxybenzene | 7% |
| 4-butoxyphenyl-4-propylcyclohexanecarboxylate | 1.5% |
| 4-methoxyphenyl-4-pentylcyclohexanecarboxylate | 1.5% |
| 4-ethoxyphenyl-4-pentylcyclohexanecarboxylate | 1% |
| 4-fluorophenyl-4-ethylcyclohexanecarboxylate | 2% |
| 4-fluorophenyl-4-propylcyclohexanecarboxylate | 2% |
| 4-fluorophenyl-4-butylcyclohexanecarboxylate | 2% |
| 4-(4-(4-ethylcyclohexyl)cyclohexyl)-1-methylbenzene | 5% |
| 4-(4-(4-propylcyclohexyl)cyclohexyl)-1-methylbenzene | 5% |
| 4-(4-(4-propylcyclohexyl)cyclohexyl)-1-propylbenzene | 8% |
| 4-(4-(4-propylcyclohexyl)cyclohexyl)-1-fluorobenzene | 3% |
| 4-(4-(4-ethylcyclohexyl)cyclohexyl)-1,2-difluorobenzene | 10% |
| 4-(4-(4-propylcyclohexyl)cyclohexyl)-1,2-difluorobenzene | 10% |
| 4-(4-(4-pentylcyclohexyl)cyclohexyl)-1,2-difluorobenzene | 6% |
| 2-fluoro-4-(4-(4-ethylcyclohexyl)cyclohexyl)benzonitrile | 3% |
| 2-fluoro-4-(4-(4-propylcyclohexyl)cyclohexyl)benzonitrile | 3% |

COMPOSITION EXAMPLE 10

| | |
|---|---|
| 4'-(4-(2-methylpropyl)cyclohexyl)-4-trifluoromethoxybiphenyl (Compound No. 1) | 3% |
| 4'-(4-(3-butylpropyl)cyclohexyl)-4-trifluoromethoxybiphenyl (Compound No. 2) | 3% |
| 4'-(4-(3-methylpentyl)cyclohexyl)-4-trifluoromethoxybiphenyl (Compound No. 44) | 3% |
| 4-(4-(4-(4-methylpentyl)cyclohexyl)cyclohexyl)-1-trifluoromethoxybenzene (Compound No. 113) | 5% |
| 4-(4-(4-(4-methylpentyl)cyclohexyl)cyclohexyl)-1-trifluoromethoxy-2-fluorobenzene (Compound No. 114) | 5% |
| 4-(4-heptylcyclohexyl)-1-fluorobenzene | 3% |
| 4-(4-(4-ethylcyclohexyl)cyclohexyl)-1,2-difluorobenzene | 12% |
| 4-(4-(4-propylcyclohexyl)cyclohexyl)-1,2-difluorobenzene | 12% |
| 4-(4-(4-pentylcyclohexyl)cyclohexyl)-1,2-difluorobenzene | 12% |
| 4-(4-(2-(4-ethylcyclohexyl)ethyl)cyclohexyl)-1,2-difluorobenzene | 6% |
| 4-(4-(2-(4-propylcyclohexyl)ethyl)cyclohexyl)-1,2-difluorobenzene | 3% |
| 4-(4-(2-(4-pentylcyclohexyl)ethyl)cyclohexyl)-1,2-difluorobenzene | 6% |
| 4'-(4-ethylcyclohexyl)-3,4-difluorobiphenyl | 3% |
| 4'-(4-propylcyclohexyl)-3,4-difluorobiphenyl | 3% |
| 4'-(4-pentylcyclohexyl)-3,4-difluorobiphenyl | 6% |
| 4-fluorophenyl-4-(4-propylcyclohexyl)cyclohexanecarboxylate | 4% |
| 4-fluorophenyl-4-(4-pentylcyclohexyl)cyclohexanecarboxylate | 4% |
| 4'-fluorobiphenylyl-4-(4-propylcyclohexyl)cyclohexanecarboxylate | 4% |
| 4'-fluorobiphenylyl-4-(4-pentylcyclohexyl)cyclohexanecarboxylate | 3% |

COMPOSITION EXAMPLE 11

| | |
|---|---|
| 4'-(4-(4-methylpentyl)cyclohexyl)-4-trifluoromethoxybiphenyl (Compound No. 80) | 10% |
| 4-(4-(4-(4-methylpentyl)cyclohexyl)cyclohexyl)-1-trifluoromethoxy-2,3-difluorobenzene (Compound No. 115) | 10% |
| 3,4-difluoro-4-cyanophenyl-4-(3-pentenyl)benzoate | 10% |
| 3-fluoro-4-cyanophenyl-4-ethoxymethylbenzoate | 3% |
| 3-fluoro-4-cyanophenyl-4-propoxymethylbenzoate | 5% |
| 4-cyanophenyl-2-fluoro-4-(4-propylcyclohexyl)benzoate | 12% |
| 4-(4-propylcyclohexyl)-1-butylcyclohexane | 8% |
| 4-(4-methoxymethylcyclohexyl)-1-propylcyclohexane | 3% |
| 4-(2-(4-butylphenyl)ethynyl)-1-ethoxybenzene | 5% |
| 2-fluoro-4-(4-ethylcyclohexyl)cyclohexyl)benzonitrile | 10% |
| 2-fluoro-4-(4-propylcyclohexyl)cyclohexyl)benzonitrile | 10% |
| 4-(2-(4-(2-(4-propylcyclohexyl)ethyl)phenyl)ethynyl)-1-ethylbenzene | 3% |
| 4-(2-(4-(2-(4-propylcyclohexyl)ethyl)phenyl)ethynyl)-1-propylbenzene | 3% |
| 4-(2-(4-(2-(4-propylcyclohexyl)ethyl)phenyl)ethynyl)-1-butylbenzene | 3% |
| 4-(2-(4-ethylphenyl)ethynyl)-1-methylbenzene | 2% |
| 4-(2-(4-methylphenyl)ethynyl)-1-hexylbenzene | 4% |
| 4-(2-(4-butylphenyl)ethynyl)-1-butylbenzene | 2% |

COMPOSITION EXAMPLE 12

| | |
|---|---|
| 4-(4-(4-(4-methylpentyl)cyclohexyl)cyclohexyl)-1-trifluoromethoxy-2-fluorobenzene (Compound No. 114) | 8% |
| 4-(4-(4-(4-methylpentyl)cyclohexyl)cyclohexyl)-1-trifluoromethoxy-2,3-difluorobenzene (Compound No. 115) | 7% |
| 4-(4-(3-butenyl)cyclohexyl)benzonitrile | 8% |
| 4-(4-(3-pentenyl)cyclohexyl)benzonitrile | 8% |
| 4-(4-propylcyclohexyl)benzonitrile | 24% |
| 4-(4-pentylcyclohexyl)benzonitrile | 10% |
| 2-fluoro-4-(4-propylcyclohexyl)benzonitrile | 6% |
| 4-cyanophenyl=4-ethylbenzoate | 3% |
| 4-(4-(4-propylcyclohexyl)cyclohexyl)-1-methylbenzene | 6% |
| 4-(4-(4-propylcyclohexyl)cyclohexyl)-1-methoxybenzene | 3% |
| 4-(4-(4-propylcyclohexyl)cyclohexyl)-1-propylbenzene | 8% |
| 4-(2-(4-(2-(4-propylcyclohexyl)ethyl)phenyl)ethynyl)-1-ethylbenzene | 3% |
| 4-(2-(4-(2-(4-propylcyclohexyl)ethyl)phenyl)ethynyl)-1-propylbenzene | 3% |
| 4-(2-(4-(2-(4-propylcyclohexyl)ethyl)phenyl)ethynyl)-1-butylbenzene | 3% |

COMPOSITION EXAMPLE 13

| | |
|---|---|
| 4-(4-(4-(4-methylpentyl)cyclohexyl)cyclohexyl)-1-trifluoromethoxybenzene (Compound No. 113) | 10% |
| 4'-(4-(5-methylhexyl)cyclohexyl)-4-trifluoromethoxybiphenyl (Compound No. 149) | 4% |
| 4'-ethyl-4-cyanobiphenyl | 4% |
| 4-(4-methoxymethylcyclohexyl)benzonitrile | 8% |
| 4-(4-ethoxymethylcyclohexyl)benzonitrile | 7% |
| 4-cyanophenyl-4-ethylbenzoate | 10% |
| 2-(4-fluorophenyl)-5-pentylpyrimidine | 7% |
| 2-(4-ethylphenyl)-5-ethylpyrimidine | 2% |
| 2-(4-ethylphenyl)-5-propylpyrimidine | 2% |
| 2-(4-ethylphenyl)-5-butylpyrimidine | 2% |
| 4-(4-(4-ethylcyclohexyl)cyclohexyl)-1-methylbenzene | 4% |
| 4-(4-(4-propylcyclohexyl)cyclohexyl)-1-methylbenzene | 4% |
| 4-(4-(4-propylcyclohexyl)cyclohexyl)-1-propylbenzene | 10% |
| 2-(4-(4-propylcyclohexyl)phenyl)-5-ethylpyrimidine | 5% |
| 2-(4-(4-propylcyclohexyl)phenyl)-5-propylpyrimidine | 5% |
| 2-(4-(4-butylcyclohexyl)phenyl)-5-butylpyrimidine | 5% |
| 2-(4'-fluorobiphenylyl)-5-propylpyrimidine | 2% |
| 2-(4'-fluorobiphenylyl)-5-butylpyrimidine | 2% |
| 2-(4'-ethylbiphenylyl)-5-hexylpyrimidine | 3% |
| 4'-(2-ethoxyethoxy)-4-iodobiphenyl | 4% |

COMPOSITION EXAMPLE 14

| | |
|---|---|
| 4'-(4-(4-methylpentyl)cyclohexyl)-4-trifluoromethoxybiphenyl (Compound No. 80) | 10% |
| 2-(3,4-difluorophenyl)-5-propylpyrimidine | 5% |
| 4-cyanaophenyl-4-ethylbenzoate | 10% |
| 4-cyanaophenyl-4-propylbenzoate | 4% |
| 2-(4-cyanophenyl)-5-propyl-1,3-dioxane | 8% |
| 2-(4-cyanophenyl)-5-butyl-1,3-dioxane | 8% |
| 4-butoxyphenyl-4-propylcyclohexanecarboxylate | 8% |
| 4-ethoxyphenyl-4-butylcyclohexanecarboxylate | 6% |
| 4-methoxyphenyl-4-pentylcyclohexanecarboxylate | 6% |
| 4-ethoxyphenyl-4-propylcyclohexanecarboxylate | 5% |
| 4-ethoxyphenyl-4-pentylcyclohexanecarboxylate | 4% |
| 4-(4-(4-propylcyclohexyl)cyclohexyl)-1-methylbenzene | 5% |
| 4'-cyanobiphenylyl-4-(4-propylcyclohexyl)cyclohexanecarboxylate | 3% |
| 4'-cyanobiphenylyl-4-(4-propylcyclohexyl)benzoate | 3% |
| 4'-cyanobiphenylyl-4-(4-pentylcyclohexyl)benzoate | 3% |
| 4-ethylphenyl-4-methoxybenzoate | 3% |
| 4-propylphenyl-4-butylcyclohexanecarboxylate | 3% |
| 4-methylphenyl-4-pentylcyclohexanecarboxylate | 3% |
| 2-(4-ethoxyphenyl)-5-hexylpyrimidine | 3% |

COMPOSITION EXAMPLE 15

| | |
|---|---|
| 4'-(4-(3-methylpentyl)cyclohexyl)-4-trifluoromethoxybiphenyl (Compound No. 44) | 5% |
| 4'-(4-(4-methylpentyl)cyclohexyl)-4-trifluoromethoxybiphenyl (Compound No. 80) | 5% |
| 4-(4-(4-(4-methylpentyl)cyclohexyl)cyclohexyl)-1-trifluoromethoxybenzene (Compound No. 113) | 10% |
| 4-(4-(4-(4-methylpentyl)cyclohexyl)cyclohexyl)-1-trifluoromethoxy-2-fluorobenzene (Compound No. 114) | 5% |
| 4-(4-propylcyclohexyl)benzoate | 15.4% |
| 4-fluorophenyl-4-pentylcyclohexanecarboxylate | 3% |
| 4-fluorophenyl-4-heptylcyclohexanecarboxylate | 3% |
| 4-fluorophenyl-4-(4-propylcyclohexyl)cyclohexanecarboxylate | 1% |
| 4-fluorophenyl-4-(4-pentylcyclohexyl)cyclohexanecarboxylate | 1% |
| 4-butoxyphenyl-4-propylcyclohexanecarboxylate | 3.2% |
| 4-ethoxyphenyl-4-butylcyclohexanecarboxylate | 2.4% |
| 4-methoxyphenyl-4-pentylcyclohexanecarboxylate | 2.4% |
| 4-ethoxyphenyl-4-propylcyclohexanecarboxylate | 2.0% |
| 4-ethoxyphenyl-4-pentylcyclohexanecarboxylate | 1.6% |
| 4-(2-(2-fluoro-4-(4-propylcyclohexyl)phenyl)ethynyl)-1-ethylbenzene | 5% |
| 4-(2-(2-fluoro-4-(4-propylcyclohexyl)phenyl)ethynyl)-1-propylbenzene | 5% |
| 4-(2-(2-fluoro-4-(4-propylcyclohexyl)phenyl)ethynyl)-1-butylbenzene | 5% |
| 4-(2-(4-(2-(4-propylcyclohexyl)ethyl)phenyl)ethynyl)-1-ethylbenzene | 3% |
| 4-(2-(4-(2-(4-propylcyclohexyl)ethyl)phenyl)ethynyl)-1-propylbenzene | 3% |
| 4-(2-(4-(2-(4-propylcyclohexyl)ethyl)phenyl)ethynyl)-1-butylbenzene | 3% |
| 4'-cyanobiphenylyl-4-(4-propylcyclohexyl)cyclohexanecarboxylate | 2% |
| 4'-cyanobiphenylyl-4-(4-pentylcyclohexyl)cyclohexanecarboxylate | 2% |
| 4'-cyanobiphenylyl-4-(4-propylcyclohexyl)benzoate | 2% |
| 4'-cyanobiphenylyl=4-(4-pentylcyclohexyl)benzoate | 2% |
| 4-fluorophenyl-4-(4-propylcyclohexylcarbonyloxy)benzoate | 3% |
| Methyl=4-(4-propylcyclohexyl)cyclohexanecarboxylate | 3% |

COMPOSITION EXAMPLE 16

| | |
|---|---|
| 4'-(4-(2-methylpropyl)cyclohexyl)-4-trifluoromethoxybiphenyl (Compound No. 1) | 3% |
| 4'-(4-(3-butylpropyl)cyclohexyl)-4-trifluoromethoxybiphenyl (Compound No. 2) | 3% |
| 4'-(4-(3-methylpentyl)cyclohexyl)-4-trifluoromethoxybiphenyl (Compound No. 44) | 3% |
| 4-(4-(4-(4-methylpentyl)cyclohexyl)cyclohexyl)-1-trifluoromethoxybenzene (Compound No. 113) | 9% |
| 4'-(4-(5-methylhexyl)cyclohexyl)-4-trifluoromethoxybiphenyl (Compound No. 149) | 3% |
| 4-(4-propylcyclohexyl)benzoate | 10% |
| 4-(4-methoxymethylcyclohexyl)benzoate | 8% |
| 4-(2-(4-ethylphenyl)ethynyl)-1-methylbenzene | 4% |
| 4-(2-(4-methylphenyl)ethynyl)-1-hexylbenzene | 8% |
| 4-(2-(4-butylphenyl)ethynyl)-1-butylbenzene | 4% |
| 4-(4-(4-propylcyclohexyl)cyclohexyl)benzonitrile | 5% |
| 4-(4-(2-(4-ethylcyclohexyl)ethyl)cyclohexyl)-1,2-difluorobenzene | 10% |
| 4-(4-(2-(4-propylcyclohexyl)ethyl)cyclohexyl)-1,2-difluorobenzene | 5% |
| 4-(4-(2-(4-pentylcyclohexyl)ethyl)cyclohexyl)-1,2-difluorobenzene | 10% |
| 4-(4-(4-propylcyclohexyl)cyclohexyl)-1-methoxybenzene | 3% |
| 4-(4-(4-propylcyclohexyl)cyclohexyl)-1-methylbenzene | 6% |
| 4-(2-(2-fluoro-4-(4-propylcyclohexyl)phenyl)ethynyl)-1-ethylbenzene | 3% |
| 4'-fluoro-4-cyanobiphenyl | 3% |

COMPOSITION EXAMPLE 17

| | |
|---|---|
| 4-(4-(4-(4-methylpentyl)cyclohexyl)cyclohexyl)-1-trifluoromethoxy-2,3-difluorobenzene (Compound No. 115) | 19% |
| 4-(4-pentylcyclohexyl)-1-fluorobenzene | 10% |
| 4-(4-heptylcyclohexyl)-1-fluorobenzene | 10% |
| 4-(4-(4-ethylcyclohexyl)cyclohexyl)-1-trifluoromethoxybenzene | 8% |
| 4-(4-(4-propylcyclohexyl)cyclohexyl)-1-trifluoromethoxybenzene | 8% |
| 4-(4-(4-pentylcyclohexyl)cyclohexyl)-1-trifluoromethoxybenzene | 8% |
| 4-(4-(4-propylcyclohexyl)cyclohexyl)-1-difluoromethoxy-2,6-difluorobenzene | 15% |
| 4-(4-(4-pentylcyclohexyl)cyclohexyl)-1-difluoromethoxy-2,6-difluorobenzene | 15% |
| 4'-(4-propylcyclohexyl)-2',6',3,4-tetrafluorobiphenyl | 5% |
| 4'-(4-pentylcyclohexyl)-2',6',3,4-tetrafluorobiphenyl | 5% |
| 4-trifluoromethoxyphenyl-4-(4-propylcyclohexy 1)cyclohexanecarboxylate | 3% |
| 4-trifluoromethoxyphenyl-4-(4-pentylcyclohexy 1)cyclohexanecarboxylate | 3% |

COMPOSITION EXAMPLE 18

| | |
|---|---|
| 4'-(4-(3-butylpropyl)cyclohexyl)-4-trifluoromethoxybiphenyl (Compound No. 2) | 4% |
| 4'-(4-(3-methylpentyl)cyclohexyl)-4-trifluoromethoxybiphenyl (Compound No. 44) | 4% |
| 4'-(4-(4-methylpentyl)cyclohexyl)-4-trifluoromethoxybiphenyl (Compound No. 80) | 4% |
| 4-(4-(4-(4-methylpentyl)cyclohexyl)cyclohexyl)-1-trifluoromethoxybenzene (Compound No. 113) | 14% |
| 4-(4-pentylcyclohexyl)-1-fluorobenzene | 8% |
| 4-(4-hexylcyclohexyl)-1-fluorobenzene | 8% |
| 4-(4-heptylcyclohexyl)-1-fluorobenzene | 8% |
| 4-(4-(4-ethylcyclohexyl)cyclohexyl)-1-trifluoromethoxybenzene | 6% |
| 4-(4-(4-propylcyclohexyl)cyclohexyl)-1-trifluoromethoxybenzene | 6% |
| 4-(4-(4-butylcyclohexyl)cyclohexyl)-1-trifluoromethoxybenzene | 6% |
| 4-(4-(4-pentylcyclohexyl)cyclohexyl)-1-trifluoromethoxybenzene | 6% |
| 4-(2-(4-(4-propylcyclohexyl)cyclohexyl)ethyl)-1-trifluoromethoxybenzene | 5% |
| 4-(2-(4-(4-pentylcyclohexyl)cyclohexyl)ethyl)-1-trifluoromethoxybenzene | 5% |
| 4'-(4-propylcyclohexyl)-3,4-difluorobiphenyl | 5% |
| 4'-(4-pentylcyclohexyl)-3,4-difluorobiphenyl | 5% |
| 2'-fluoro-4'-(4-propylcyclohexyl)-4-(4-propylcyclohexyl)biphenyl | 3% |
| 2'-fluoro-4'-(4-pentylcyclohexyl)-4-(4-propylcyclohexyl)biphenyl | 3% |

COMPOSITION EXAMPLE 19

| | |
|---|---|
| 4'-(4-(3-methylpentyl)cyclohexyl)-4-trifluoromethoxybiphenyl (Compound No. 44) | 5% |
| 4'-(4-(4-methylpentyl)cyclohexyl)-4-trifluoromethoxybiphenyl (Compound No. 80) | 5% |
| 4-(4-(4-(4-methylpentyl)cyclohexyl)cyclohexyl)-1-trifluoromethoxybenzene (Compound No. 113) | 5% |
| 4'-(4-(5-methylhexyl)cyclohexyl)-4-trifluoromethoxybiphenyl (Compound No. 149) | 5% |
| 4-(4-(4-(4-methylpentyl)cyclohexyl)cyclohexyl)-1-trifluoromethoxy-2-fluorobenzene (Compound No. 114) | 5% |
| 4-(4-(2-propenyl)cyclohexyl)benzonitrile | 3% |
| 4'-butyl-4-ethylbiphenyl | 3% |
| 4'-propyl-4-cyanobiphenyl | 5% |
| 4'-pentyl-4-cyanobiphenyl | 5% |
| 2-fluoro-4-(4-ethylcyclohexyl)benzonitrile | 5% |
| 4-(2-(4-propylcyclohexyl)ethyl)-1-ethoxybenzene | 4% |
| 4-(2-(4-pentylcyclohexyl)ethyl)-1-propoxybenzene | 8% |
| 4-cyanophenyl=4-propylbenzoate | 5% |
| 4-methoxyphenyl=4-pentylcyclohexanecarboxylate | 6% |
| 4-propoxyphenyl=4-pentylcyclohexanecarboxylate | 6% |
| 1"-pentyl-4-cyanoterphenyl | 3% |
| 2-(4-cyanophenyl)-5-(4-butylphenyl)pyrimidine | 3% |
| 2-(4-pentylphenyl)-5-(4-butylphenyl)pyrimidine | 3% |
| 4-(2-(4-(4-pentylcyclohexyl)phenyl)ethyl)-1-butylbenzene | 3% |
| 4-(2-(4'-(4-pentylcyclohexyl)biphenylyl)ethyl)-1-propylbenzene | 3% |
| 4-(4-(1-propenyl)cyclohexyl)-1-methoxymethylcyclohexane | 5% |
| 4'-(4-(3-pentenyl)cyclohexyl)-4-propylbiphenyl | 5% |

COMPOSITION EXAMPLE 20

| | |
|---|---|
| 4-(4-(4-(4-methylpentyl)cyclohexyl)cyclohexyl)-1-trifluoromethoxybenzene (Compound No. 113) | 10% |
| 4-(4-(4-(4-methylpentyl)cyclohexyl)cyclohexyl)-1-trifluoromethoxy-2-fluorobenzene (Compound No. 114) | 10% |
| 3,4-difluorophenyl-4-butylcyclohexanecarboxylate | 5% |
| 3,4-difluorophenyl-4-pentylcyclohexanecarboxylate | 5% |
| 3-fluoro-4-cyanophenyl-4-ethylbenzoate | 4% |
| 3-fluoro-4-cyanophenyl-4-propylbenzoate | 4% |
| 3-fluoro-4-cyanophenyl-4-butylbenzoate | 6% |
| 3-fluoro-4-cyanophenyl-4-pentylbenzoate | 6% |
| 2-fluoro-4-(4-(3-methoxypropyl)cyclohexyl)benzonitrile | 6% |
| 3,4-difluorophenyl-4-(4-propylcyclohexyl)cyclohexanecarboxylate | 4% |
| 3,4-difluorophenyl-4-(4-pentylcyclohexyl)cyclohexanecarboxylate | 4% |
| 3-fluoro-4-cyanophenyl-4-(4-ethylcyclohexyl)benzoate | 5% |
| 3-fluoro-4-cyanophenyl-4-(4-propylcyclohexyl)benzoate | 5% |
| 3-fluoro-4-cyanophenyl-4-(4-butylcyclohexyl)benzoate | 5% |
| 3-fluoro-4-cyanophenyl-4-(4-pentylcyclohexyl)benzoate | 5% |
| 4-(2-(4-(4-propylcyclohexyl)phenyl)ethynyl)-1-ethylbenzene | 10% |
| 4-(4-(3-butenyl)cyclohexyl)-1-propylcyclohexane | 3% |
| 4-(4-(3-butenyl)cyclohexyl)cyclohexyl)-1-methylbenzene | 3% |

Compounds of the present invention expressed by the general formula (1) can easily be synthesized by using usual organic synthesis process described in "Organic Synthesis", "Organic Reactions", "Shin-Jikken Kagaku Kouza (Course of New Experimental Chemistry)" and other reference books in combination. Some of the typical reaction paths are shown below:

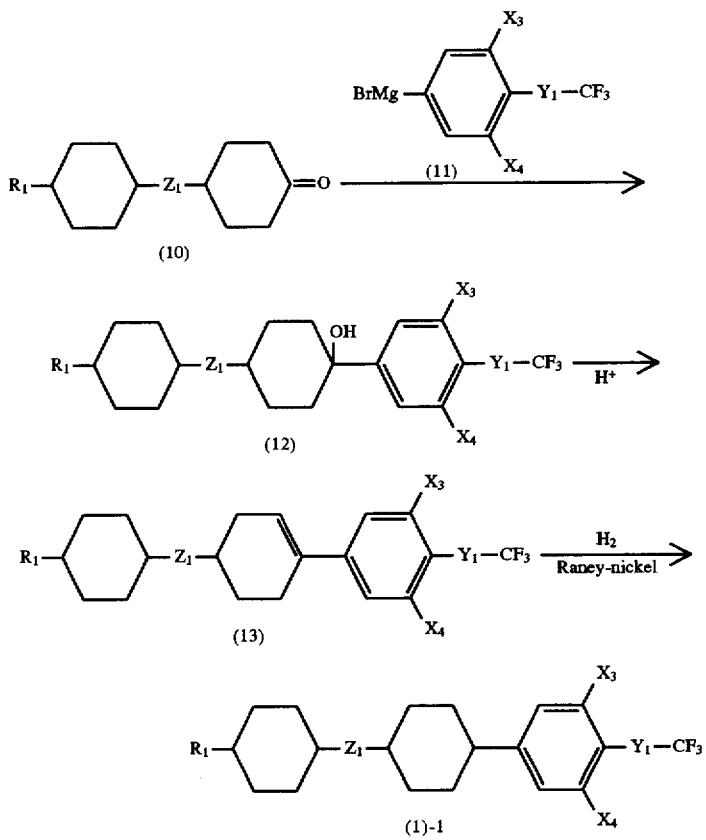

Grignard reagent (11) of a bromobenzene derivative produced by the method described in reference books is reacted with a cyclohexane derivative (10) to obtain an alcohol derivative (12). Alcohol derivative (12) is subjected to an acid treatment to convert it to a cyclohexene derivative (13), and then subjected to a hydrogenation in the presence of a catalyst to produce Compounds (1)-1 expressed by the general formula (1) wherein ring A is cyclohexane ring, $Z_2$ is a single bond. As the catalyst to be used for the hydrogenation, catalysts usually placed on the market such as Pd/C, Pt/C, and Raney-nickel are sufficient. However, Raney nickel is preferable from the viewpoint of its excellent cis/trans selectivity of cyclohexane rings in the compounds (1)-1 to be produced.

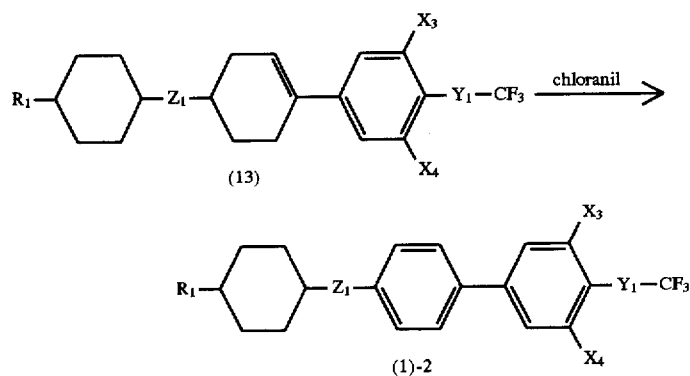

Compounds (1)-2 which are included in the compounds expressed by the general formula (1) wherein ring A is unsubstituted benzene ring and $Z_2$ is a single bond can be produced by treating the cyclohexane derivative (13) with a dehydrogenating agent such as chloranil.

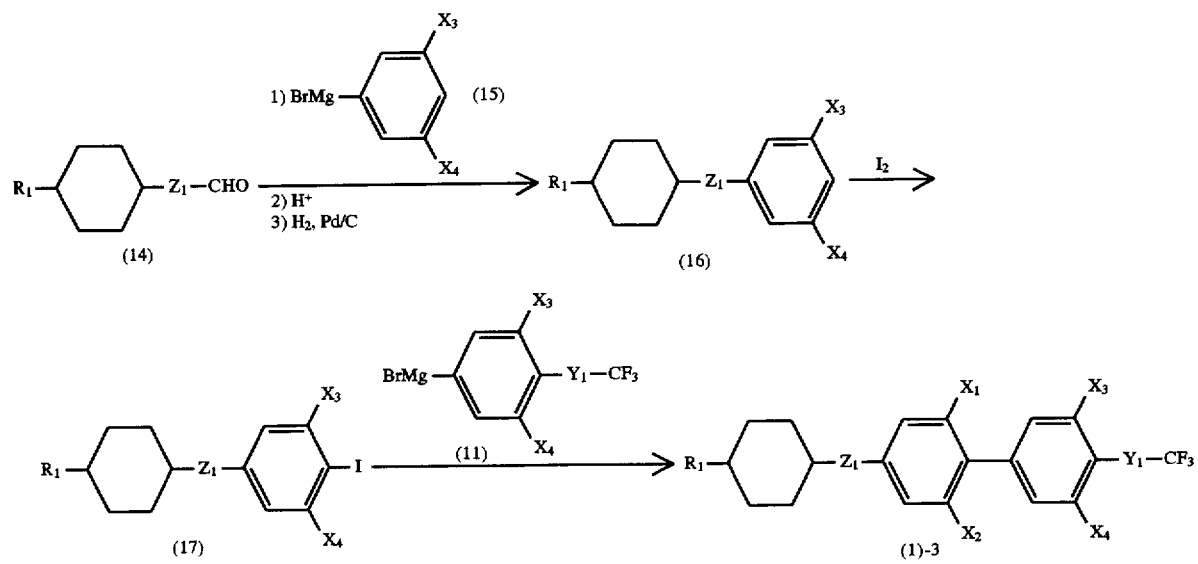

Grignard reagent (15) of a bromobenzene derivative which is commercially available is reacted to an aldehyde

(14) and subjected to an acid treatment and hydrogenation to obtain compound (16). Compound (16) is converted to an iodide (17)i This compound is reacted with Grignard reagent (11) and then subjected to a cross coupling reaction in the presence of a catalyst to obtain Compounds (1)-3 which are included in the compounds expressed by the general formula (1) wherein ring A is substituted benzene ring. As the catalyst to be used for the cross coupling reaction, palladium or nickel catalyst can preferably be used.

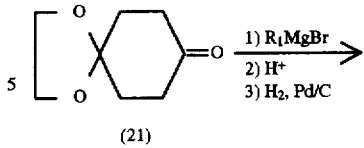

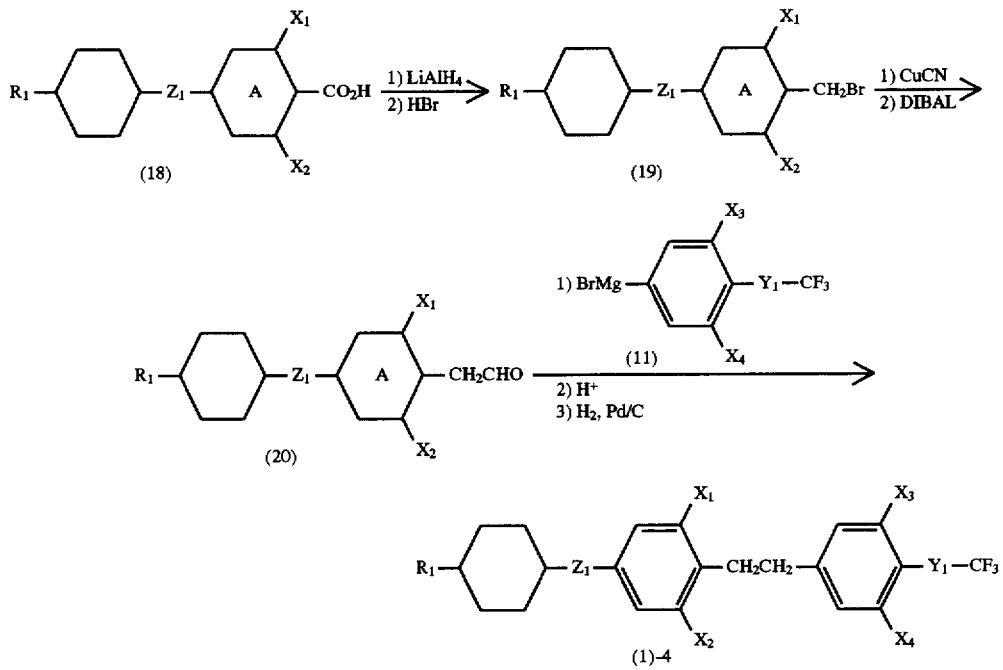

Lithium aluminum hydride and hydrogen bromide are reacted to carboxylic acid (18) in turn to obtain a bromide (19). The bromide (19) is made into a cyanide and then subjected to a hydrogenation with diisobutylaluminum hydride for reduction to obtain an aldehyde (20).

Grignard reagent (11) is reacted to the aldehyde (20), and then further subjected to an acid treatment and hydrogenation in turn to obtain compound (1)-4 which is included in the compounds expressed by the general formula (1) wherein $Z_2$ is 1,2-ethylene group.

Cyclohexanone derivative (10) mentioned above can preferably be produced, for instance, by the following method. That is, the Grignard reagent prepared from various branched alkylbromides is reacted to cyclohexanedione monoacetal (21), and subjected to an acid treatment and hydrogenation in turn to obtain 4-substituted cyclohexanone (22). This compound is reacted with Grignard reagent of anisbromide or Grignard reagent of methoxyphenethylbromide, and subjected to an acid treatment and hydrogenation in turn to obtain an anisole derivative (24). Anisole derivative (24) is subjected to a demethylation with hydrobromic acid, and then subjected to a hydrogenation and oxidization in turn to obtain a cyclohexanone derivative (10).

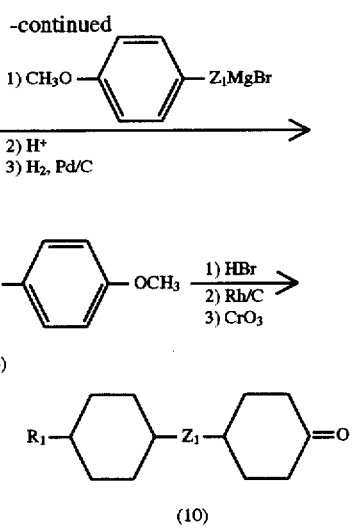

Phosphonium salt obtained from methoxymethylchloride is reacted to the substituted cyclohexanone (22) under a basic condition, and then further subjected to an acid treatment to obtain compound (14-1) which corresponds to an aldehyde (14) in which $Z_2$ is a single bond. Compound (14-1) is subjected to two carbons homologation reaction mentioned above to obtain compound (14-2) which corresponds to an aldehyde (14) in which $Z_2$ is 1,2-ethylene group.

Carboxylic acids (18) can be produced by the following method. That is, the compound (18-1) which corresponds to a carboxylic acid (18) in which ring A is benzene ring can be produced by reacting copper cyanide to the iodide isomer (17) to make it to a cyanide, and then further subjecting it to an acid treatment or base treatment to hydrolyze.

Compounds (18-2) which corresponds to a carboxylic acid (18) in which ring A is cyclohexane ring can be produced by reacting a phosphonium salt obtained from methoxymethylchloride to a cyclohexanone derivative (10), and then further subjecting it to an acid treatment.

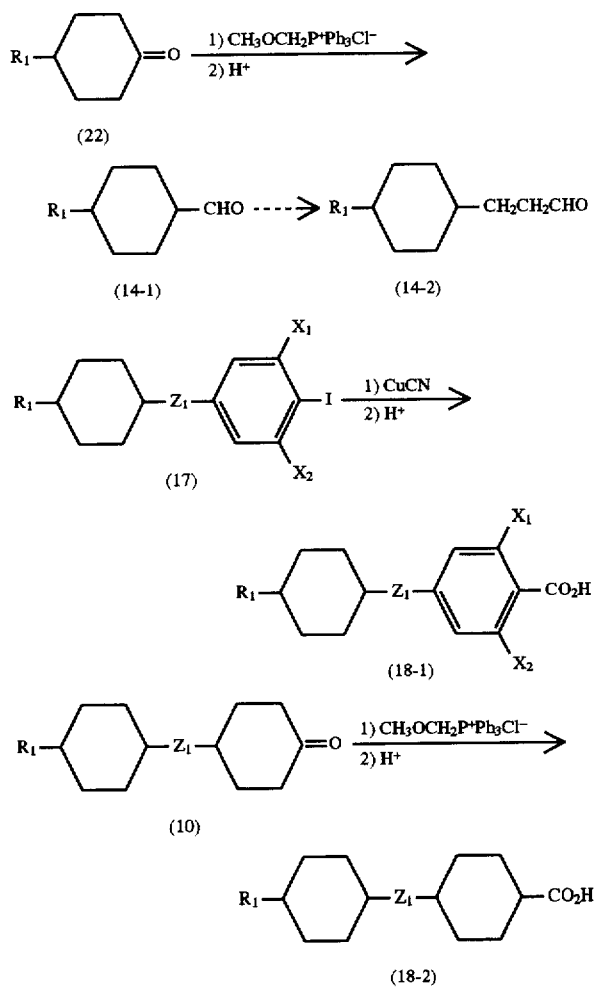

Liquid crystalline compounds of the present invention expressed by the general formula (1)

1) are excellent in miscibility with other liquid crystalline compounds, particularly in miscibility at low temperatures,
2) have a large positive value of dielectric anisotropy,
3) have an extremely low viscosity, and
4) have an extremely high specific resistance (high voltage holding ratio) and an excellent UV stability.

Accordingly, liquid crystal compositions having excellent physical properties can be obtained by using the compounds of the present invention having such excellent characteristics.

EXAMPLES

Process for producing and the method for using the compounds of the present invention are explained below in more detail with reference to Examples. In each Example, C represents a crystal, N represents a nematic phase, S represents a smectic phase, and I represents an isotropic liquid, and the unit of phase transition temperature is °C.

Example 1

Preparation of 4-(4-(4-(4-methylpentyl)cyclohexyl) cyclohexyl)-1-trifluoromethoxybenzene (Compound expressed by the general formula (1) in which $R_1$ is 4-methylpentyl group, ring A is 1,4-cyclohexane ring, $Z_1$ and $Z_2$ are a single bond, each of $X_1$, $X_2$, $X_3$, and $X_4$ is hydrogen atom, and $Y_1$ is oxygen atom; Compound No. 113)

Solution of 4-trifluoromethoxybromobenzene (50 mmol) in THF (tetrahydrofuran) (100 ml) was added dropwise to a mixture of sufficiently dried magnesium (50 mmol) and THF (5 ml) under a reflux condition to obtain a corresponding gray uniform solution of Grignard reagent, followed by dropwise adding a solution of 4-(4-(4-methylpentyl) cyclohexyl)cyclohexanone (50 mmol) in THF (50 ml) prepared according to the method described in Japanese Patent Publication No. 62-39136 at a temperature lower than 0° C., and then stirred at room temperature for 3 hours. Slowly adding to the solution a saturated aqueous solution (100 ml) of ammonium chloride and toluene (200 ml), sufficiently stirred, and allowed to stand. Organic layer was separated, sufficiently washed with water until the layer became neutral, and dried over anhydrous magnesium sulfate.

Distilling off the solvent was distilled off under a reduced pressure, a crude product was obtained, adding with toluene (200 ml) and p-toluene sulfonic acid (2.5 mmol), and heated to reflux for 3 hours while performing dehydration. After allowing the reaction solution to cool, a saturated aqueous solution of sodium bicarbonate was added thereto, and sufficiently stirred. Organic layer was dried over anhydrous magnesium sulfate. After the solvent was distilled off, a crude product was recrystallized from ethanol which is three times by volume as much as the crude product in amount to obtain a white solid of 4-(4-(4-methylpentyl)cyclohexyl)-1-(4-trifluoromethoxyphenyl)-cyclohexene (24 mmol; yield 48%).

Mixture of 4-(4-(4-methylpentyl)cyclohexyl)-1-(4-trifluoromethoxyphenyl)cyclohexene (24 mmol), Raney nickel (0.36 g), and ethanol (30 ml) was stirred at room temperature under hydrogen atmosphere for 5 hours. Catalyst was separated off, the solvent was distilled off. The crude product thus obtained was subjected to a silica gel column chromatography (eluate: toluene) and recrystallized from ethanol which is 5 times by volume as much as the crude product in amount to obtain the captioned compound (10.5 mmol; yield 44%). This product showed the phase transition temperatures as follows:

S–N point 82.3° to 83.2° C.
N–I point 125.6° to 126.3° C.

Data of various kinds of spectra well supported the structure of the compound.

1H-NMR: δ (ppm): 7.42 (dd, 4H), 2.51 (t1H), 1.99 to 0.84 (m, 32H)

GC-MS: 410 (M+)

Example 2

Following compounds were produced according to the method in Example 1 and examples of production mentioned above. Compound mentioned in Example 1 is shown again.

Compound No. 1
4'-(4-(2-methylpropyl)cyclohexyl)-4-trifluoromethoxybiphenyl
S–N point 102.9° to 104.1° C.
N–I point 111.2° to 114.2° C.

Compound No. 2
4'-(4-(3-methylbutyl)cyclohexyl)-4-trifluoromethoxybiphenyl
S–I point 141.7° to 143.6° C.

Compound No. 3
4'-(4-(1-methylpentyl)cyclohexyl)-4-trifluoromethoxybiphenyl

Compound No. 4
4'-(4-(2-methylpentyl)cyclohexyl)-4-trifluoromethoxybiphenyl

Compound No. 5
4-(4-(4-(3-methylpentyl)cyclohexyl)cyclohexyl)-1-trifluoromethylbenzene Compound No. 6
4-(4-(4-(3-methylpentyl)cyclohexyl)cyclohexyl)-1-trifluoromethyl-2-fluorobenzene Compound No. 7
4-(4-(4-(3-methylpentyl)cyclohexyl)cyclohexyl)-1-trifluoromethyl-2,6-difluorobenzene Compound No. 8
4'-(4-(3-methylpentyl)cyclohexyl)-4-trifluoromethylbiphenyl Compound No. 9
4'-(4-(3-methylpentyl)cyclohexyl)-3-fluoro-4-trifluoromethylbiphenyl Compound No. 10
4'-(4-(3-methylpentyl)cyclohexyl)-3,5-difluoro-4-trifluoromethylbiphenyl Compound No. 11
2'-fluoro-4'-(4-(3-methylpentyl)cyclohexyl)-4-trifluoromethylbiphenyl Compound No. 12
2'-fluoro-4'-(4-(3-methylpentyl)cyclohexyl)-3-fluoro-4-trifluoromethylbiphenyl Compound No. 13
2'-fluoro-4'-(4-(3-methylpentyl)cyclohexyl)-3,5-difluoro-4-trifluoromethylbiphenyl Compound No. 14
2',6'-difluoro-4'-(4-(3-methylpentyl)cyclohexyl)-4-trifluoromethylbiphenyl Compound No. 15
2',6'-difluoro-4'-(4-(3-methylpentyl)cyclohexyl)-3-fluoro-4-trifluoromethylbiphenyl Compound No. 16
2',6'-difluoro-4'-(4-(3-methylpentyl)cyclohexyl)-3,5-difluoro-4-5trifluoromethylbiphenyl Compound No. 17
4-(4-(2-(4-(3-methylpentyl)cyclohexyl)ethyl)cyclohexyl)-1-trifluoromethylbenzene Compound No. 18
4-(4-(2-(4-(3-methylpentyl)cyclohexyl)ethyl)cyclohexyl)-1-trifluoromethyl-2-fluorobenzene Compound No. 19
4-(4-(2-(4-(3-methylpentyl)cyclohexyl) ethyl)cyclohexyl)-1-trifluoromethyl-2,6-difluorobenzene Compound No. 20
4'(2-(4-(3-methylpentyl)cyclohexyl) ethyl)-4-trifluoromethylbiphenyl Compound No. 21
4'(2-(4-(3-methylpentyl)cyclohexyl) ethyl)-3-fluoro-4-trifluoromethylbiphenyl Compound No. 22
4'(2-(4-(3-methylpentyl)cyclohexyl) ethyl)-3,5-difluoro-4-trifluoromethylbiphenyl Compound No. 23
2'-fluoro-4'-(2-(4-(3-methylpentyl)cyclohexyl) ethyl)-4-trifluoromethylbiphenyl Compound No. 24
2'-fluoro-4'-(2-(4-(3-methylpentyl)cyclohexyl) ethyl)-3-fluoro-4-trifluoromethylbiphenyl Compound No. 25
2'-fluoro-4'-(2-(4-(3-methylpentyl)cyclohexyl) ethyl)-3,5-difluoro-4-trifluoromethylbiphenyl Compound No. 26
2',6'-difluoro-4'-(2-(4-(3-methylpentyl)cyclohexyl) ethyl)-4-trifluoromethylbiphenyl Compound No. 27
2',6'-difluoro-4'-(2-(4-(3-methylpentyl)cyclohexyl) ethyl)-3-fluoro-4-trifluoromethylbiphenyl Compound No. 28
2',6'-difluoro-4'-(2-(4-(3-methylpentyl)cyclohexyl) ethyl)-3,5-difluoro-4-trifluoromethylbiphenyl Compound No. 29
4-(2-(4-(4-(3-methylpentyl)cyclohexyl)cyclohexyl) ethyl)-1-trifluoromethylbenzene Compound No. 30
4-(2-(4-(4-(3-methylpentyl)cyclohexyl)cyclohexyl)ethyl)-1-trifluoromethyl-2-fluorobenzene Compound No. 31
4-(2-(4-(4-(3-methylpentyl)cyclohexyl)cyclohexyl) ethyl)-1-trifluoromethyl-2,6-difluorobenzene Compound No. 32
4-(2-(4-(4-(3-methylpentyl)cyclohexyl)phenyl) ethyl)-1-trifluoromethylbenzene Compound No. 33
4-(2-(4-(4-(3-methylpentyl)cyclohexyl) phenyl) ethyl)-1-trifluoromethyl-2-fluorobenzene Compound No. 34
4-(2-(4-(4-(3-methylpentyl)cyclohexyl) phenyl) ethyl)-1-trifluoromethyl-2,6-difluorobenzene Compound No. 35
4-(2-(2-fluoro-4-(4-(3-methylpentyl)cyclohexyl) phenyl) ethyl)-1-trifluoromethylbenzene Compound No. 36
4-(2-(2-fluoro-4-(4-(3-methylpentyl)cyclohexyl) phenyl) ethyl)-1-trifluoromethyl-2-fluorobenzene Compound No. 37
4-(2-(2-fluoro-4-(4-(3-methylpentyl)cyclohexyl) phenyl) ethyl)-1-trifluoromethyl-2,6-difluorobenzene Compound No. 38
4-(2-(2,6-difluoro-4-(4-(3-methylpentyl)cyclohexyl)-phenyl)ethyl)-1-trifuoromethylbenzene Compound No. 39
4-(2-(2,6-difluoro-4-(4-(3-methylpentyl)cyclohexyl) phenyl)ethyl)-1-trifluoromethyl-2-fluorobenzene Compound No. 40
4-(2-(2,6-difluoro-4-(4-(3-methylpentyl)cyclohexyl) phenyl)ethyl)-1-trifluoromethyl-2,6-difluorobenzene Compound No. 41
4-(4-(4-(3-methylpentyl)cyclohexyl)cyclohexyl)-1-trifluoromethoxybenzene Compound No. 42
4-(4-(4-(3-methylpentyl)cyclohexyl)cyclohexyl)-1-trifluoromethoxy-2-fluorobenzene Compound No. 43
4-(4-(4-(3-methylpentyl)cyclohexyl)cyclohexyl)-1-trifluoromethoxy-2,6-difluorobenzene Compound No. 44
4'-(4-(3-methylpentyl)cyclohexyl)-4-trifluoromethoxybiphenyl S-I point 125.7° to 126.4° C.

Compound No. 45
4'-(4-(3-methylpentyl)cyclohexyl)-3-fluoro-4-trifluoromethoxybiphenyl Compound No. 46
4'-(4-(3-methylpentyl)cyclohexyl)-3,5-difluoro-4-trifluoromethoxybiphenyl Compound No. 47
2'-fluoro-4'-(4-(3-methylpentyl)cyclohexyl)-4-trifluoromethoxybiphenyl Compound No. 48
2'-fluoro-4'-(4-(3-methylpentyl)cyclohexyl)-3-fluoro-4-trifluoromethoxybiphenyl Compound No. 49
2'-fluoro-4'-(4-(3-methylpentyl)cyclohexyl)-3,5-difluoro-4-trifluoromethoxybiphenyl Compound No. 50
2'6'-difluoro-4'-(4-(3-methylpentyl)cyclohexyl)-4-trifluoromethoxybiphenyl Compound No. 51
2'6'-difluoro-4'-(4-(3-methylpentyl)cyclohexyl)-3-fluoro-4-trifluoromethoxybiphenyl Compound No. 52
2'6'-difluoro-4'-(4-(3-methylpentyl)cyclohexyl)-3,5-difluoro-4-trifluoromethoxybiphenyl Compound No. 53
4-(4-(2-(4-(3-methylpentyl)cyclohexyl) ethyl) cyclohexyl)-1-trifluoromethoxybenzene Compound No. 54
4-(4-(2-(4-(3-methylpentyl)cyclohexyl)ethyl)cyclohexyl)-1-trifluoromethoxy-2-fluorobenzene Compound No. 55
4-(4-(2-(4-(3-methylpentyl)cyclohexyl)ethyl)cyclohexyl)-1-trifluoromethoxy-2,6-difluorobenzene Compound No. 56
4'-(2-(4-(3-methylpentyl)cyclohexyl)ethyl)-4-trifluoromethoxybiphenyl Compound No. 57
4'-(2-(4-(3-methylpentyl)cyclohexyl)ethyl)-3-fluoro-4-trifluoromethoxybiphenyl Compound No. 58
4'-(2-(4-(3-methylpentyl)cyclohexyl)ethyl)-3,5-difluoro-4-trifluoromethoxybiphenyl Compound No. 59
2'-fluoro-4'-(2-(4-(3-methylpentyl)cyclohexyl)ethyl)trifluoromethoxybipehnyl Compound No. 60
2'-fluoro-4'-(2-(4-(3-methylpentyl)cyclohexyl)ethyl)-3-fluoro-4-trifluoromethoxybipehnyl Compound No. 61
2'-fluoro-4'-(2-(4-(3-methylpentyl)cyclohexyl)ethyl)-3,5-difluoro-4-trifluoromethoxybipehnyl Compound No. 62
2',6'-difluoro-4'-(2-14-(3-methylpentyl)cyclohexyl)ethyl)-4-trifluoromethoxybiphenyl Compound No. 63
2',6'-difluoro-4'-(2-(4-(3-methylpentyl)cyclohexyl)ethyl)-3-fluoro-4-trifluoromethoxybiphenyl Compound No. 64
2',6'-difluoro-4'-(2-(4-(3-methylpentyl)cyclohexyl)ethyl)-3,5-difluoro-4-trifluoromethoxybiphenyl Compound No. 65
4-(2-(4-(4-(3-methylpentyl)cyclohexyl)cyclohexyl)ethyl)-1-trifluoromethoxybenzene Compound No. 66
4-(2-(4-(4-(3-methylpentyl)cyclohexyl)cyclohexyl)ethyl)-1-trifluoromethoxy-2-fluorobenzene Compound No. 67
4-(2-(4-(4-(3-methylpentyl)cyclohexyl)cyclohexyl)ethyl)-1-trifluoromethoxy-2,6-difluorobenzene Compound No. 68
4-(2-(4-(4-(3-methylpentyl)cyclohexyl)phenyl)ethyl)-1-trifluoromethoxybenzene Compound No. 69
4-(2-(4-(4-(3-methylpentyl)cyclohexyl)phenyl)ethyl)-1-trifluoromethoxy-2-fluorobenzene Compound No. 70
4-(2-(4-(4-(3-methylpentyl)cyclohexyl) phenyl)ethyl)-1-trifluoromethoxy-2,6-difluorobenzene Compound No. 71
4-(2-(2-fluoro-4-(4-(3-methylpentyl)cyclohexyl) phenyl)ethyl)-1-trifluoromethoxybenzene Compound No. 72
4-(2-(2-fluoro-4-(4-(3-methylpentyl)cyclohexyl)phenyl)ethyl)-1-trifluoromethoxy-2-fluorobenzene Compound No. 73
4-(2-(2-fluoro-4-(4-(3-methylpentyl)cyclohexyl) phenyl)ethyl)-1-trifluoromethoxy-2,6-difluorobenzene Compound No. 74
4-(2-(2,6-difluoro-4-(4-(3-methylpentyl)cyclohexyl) phenyl)ethyl)-1-trifluoromethoxybenzene Compound No. 75
4-(2-(2,6-difluoro-4-(4-(3-methylpentyl)cyclohexyl) phenyl)ethyl)-1-trifluoromethoxy-2-fluorobenzene Compound No. 76
4-(2-(2,6-difluoro-4-(4-(3-methylpentyl)cyclohexyl) phenyl)ethyl)-1-trifluoromethoxy-2,6-difluorobenzene Compound No. 77
4-(4-(4-(4-methylpentyl)cyclohexyl)cyclohexyl)-1-trifluoromethylbenzene Compound No. 78
4-(4-(4-(4-methylpentyl)cyclohexyl)cyclohexyl)-1-trifluoromethyl-2-fluorobenzene Compound No. 79
4-(4-(4-(4-methylpentyl)cyclohexyl)cyclohexyl)-1-trifluoromethyl-2,6-difluorobenzene Compound No. 80
4'-(4-(4-methylpentyl)cyclohexyl)-4-trifluoromethylbiphenyl S-I point 107.5° to 108.1° C.

Compound No. 81
4'-(4-(4-methylpentyl)cyclohexyl)-3-fluoro-4-trifluoromethylbiphenyl Compound No. 82
4'-(4-(4-methylpentyl)cyclohexyl)-3,5-difluoro-4-trifluoromethylbiphenyl Compound No. 83
2'-fluoro-4'-(4-(4-methylpentyl)cyclohexyl)-4-trifluoromethylbiphenyl Compound No. 84
2'-fluoro-4'-(4-(4-methylpentyl)cyclohexyl)-3-fluoro-4-trifluoromethylbiphenyl
Compound No. 85
2-fluoro-4'-(4-(4-methylpentyl)cyclohexyl)-3,5-difluoro-4-trifluoromethylbiphenyl
Compound No. 86
2',6'-difluoro-4'-(4-(4-methylpentyl)cyclohexyl)-4-trifluoromethylbiphenyl
Compound No. 87
2',6'-difluoro-4'-(4-(4-methylpentyl)cyclohexyl)-3-fluoro-4-trifluoromethylbiphenyl
Compound No. 88
2', 6'-difluoro-4 '-(4-(4-methylpentyl)cyclohexyl)-3,5-difluoro-4-trifluoromethylbiphenyl
Compound No. 89
4-(4-(2-(4-(4-methylpentyl)cyclohexyl)ethyl)cyclohexyl)-1-trifluoromethylbenzene
Compound No. 90
4-(4-(2-(4-(4-methylpentyl)cyclohexyl)ethyl)cyclohexyl)-1-trifluoromethyl-2-fluorobenzene
Compound No. 91
4-(4-(2-(4-(4-methylpentyl)cyclohexyl)ethyl)cyclohexyl)-1-trifluoromethyl-2,6-difluorobenzene
Compound No. 92
4'-(2-(4-(4-methylpentyl)cyclohexyl)ethyl)-4-trifluoromethylbiphenyl
Compound No. 93
4'-(2-(4-(4-methylpentyl)cyclohexyl)ethyl)-3-fluoro-4-trifluoromethylbiphenyl
Compound No. 94
4'-(2-(4-(4-methylpentyl)cyclohexyl)ethyl)-3,5-difluoro-4-trifluoromethylbiphenyl
Compound No. 95
2'-fluoro-4'-(2-(4-(4-methylpentyl)cyclohexyl)ethyl)-4-trifluoromethylbiphenyl
Compound No. 96
2'-fluoro-4'-(2-(4-(4-methylpentyl)cyclohexyl)ethyl)-3-fluoro-4-trifluoromethylbiphenyl
Compound No. 97
2'-fluoro-4'-(2-(4-(4-methylpentyl)cyclohexyl)ethyl)-3,5-difluoro-4-trifluoromethylbiphenyl
Compound No. 98
2',6'-difluoro-4'-(2-(4-(4-methylpentyl)cyclohexyl)ethyl)-4-trifluoromethylbiphenyl
Compound No. 99
2',6'-difluoro-4'-(2-(4-(4-methylpentyl)cyclohexyl)ethyl)-3-fluoro-4-trifluoromethylbiphenyl
Compound No. 100
2',6'-difluoro-4'-(2-(4-(4-methylpentyl)cyclohexyl)ethyl)-3,5-difluoro-4-trifluoromethylbiphenyl
Compound No. 101
4-(2-(4-(4-(4-methylpentyl)cyclohexyl)cyclohexyl)ethyl)-1-trifluoromethylbenzene
Compound No. 102
4-(2-(4-(4-(4-methylpentyl)cyclohexyl)cyclohexyl)ethyl)-1-trifluoromethyl-2-fluorobenzene
Compound No. 103
4-(2-(4-(4-(4-methylpentyl)cyclohexyl)cyclohexyl)ethyl)-1-trifluoromethyl-2,6-difluorobenzene
Compound No. 104
4-(2-(4-(4-(4-methylpentyl)cyclohexyl)phenyl)ethyl)-1-trifluoromethylbenzene
Compound No. 105
4-(2-(4-(4-(4-methylpentyl)cyclohexyl)phenyl)ethyl)-1-trifluoromethyl-2-fluorobenzene
Compound No. 106
4-(2-(4-(4-(4-methylpentyl)cyclohexyl)phenyl)ethyl)-1-trifluoromethyl-2,6-difluorobenzene
Compound No. 107
4-(2-(2-fluoro-4-(4-(4-methylpentyl)cyclohexyl)phenyl)ethyl)-1-trifluoromethylbenzene
Compound No. 108
4-(2-(2-fluoro-4-(4-(4-methylpentyl)cyclohexyl)phenyl)ethyl)-1-trifluoromethyl-2-fluorobenzene
Compound No. 109
4-(2-(2-fluoro-4-(4-(4-methylpentyl)cyclohexyl)phenyl)ethyl)-1-trifluoromethyl-2,6-difluorobenzene
Compound No. 110
4-(2-(2,6-difluoro-4-(4-(4-methylpentyl)cyclohexyl)phenyl)ethyl)-1-trifluoromethylbenzene
Compound No. 111
4-(2-(2,6-difluoro-4-(4-(4-methylpentyl)cyclohexyl)phenyl)ethyl)-1-trifluoromethyl-2-fluorobenzene
Compound No. 112
4-(2-(2,6-difluoro-4-(4-(4-methylpentyl)cyclohexyl)phenyl)ethyl)-1-trifluoromethyl-2,6-difluorobenzene
Compound No. 113
4-(4-(4-(4-methylpentyl)cyclohexyl)cyclohexyl)-1-trifluoromethoxybenzene S-N point 82.3° to 83.2° C. N-I point 125.6° to 126.3° C.
Compound No. 114
4-(4-(4-(4-methylpentyl)cyclohexyl)cyclohexyl)-1-trifluoromethoxy-2-fluorobenzene
Compound No. 115
4-(4-(4-(4-methylpentyl)cyclohexyl)cyclohexyl)-1-trifluoromethoxy-2,3-difluorobenzene
Compound No. 116
4'-(4-(4-methylpentyl)cyclohexyl)-4-trifluoromethoxybiphenyl
Compound No. 117
4'-(4-(4-methylpentyl)cyclohexyl)-3-fluoro-4-trifluoromethoxybiphenyl
Compound No. 118
4'-(4-(4-methylpentyl)cyclohexyl)-3,5-difluoro-4-trifluoromethoxybiphenyl
Compound No. 119
2'-fluoro-4'-(4-(4-methylpentyl)cyclohexyl)-4-trifluoromethoxybiphenyl
Compound No. 120
2'-fluoro-4'-(4-(4-methylpentyl)cyclohexyl)-3-fluoro-4-trifluoromethoxybiphenyl
Compound No. 121
2'-fluoro-4'-(4-(4-methylpentyl)cyclohexyl)-3,5-difluoro-4-trifluoromethoxybiphenyl
Compound No. 122
2',6'-difluoro-4'-(4-(4-methylpentyl)cyclohexyl)-4-trifluoromethoxybiphenyl
Compound No. 123
2',6'-difluoro-4'-(4-(4-methylpentyl)cyclohexyl)-3-fluoro-4-trifluoromethoxybiphenyl
Compound No. 124
2',6'-difluoro-4'-(4-(4-methylpentyl)cyclohexyl)-3,5-difluoro-4-trifluoromethoxybiphenyl
Compound No. 125
4-(4-(2-(4-(4-methylpentyl)cyclohexyl)ethyl)cyclohexyl)-1-trifluoromethoxybenzene Compound No. 126
4-(4-(2-(4-(4-methylpentyl)cyclohexyl)ethyl)cyclohexyl)-1-trifluoromethoxy-2-fluorobenzene Compound No. 127
4-(4-(2-(4-(4-methylpentyl)cyclohexyl)ethyl)cyclohexyl)-1-trifluoromethoxy-2,6-difluorobenzene Compound No. 128
4'-(2-(4-(4-methylpentyl)cyclohexyl)ethyl)-4-trifluoromethoxybiphenyl Compound No. 129
4'-(2-(4-(4-methylpentyl)cyclohexyl)ethyl)-3-fluoro-4-trifluoromethoxybiphenyl Compound No. 130
4'-(2-(4-(4-methylpentyl)cyclohexyl)ethyl)-3,5-difluoro-4-trifluoromethoxybiphenyl Compound No. 131
2'-fluoro-4'-(2-(4-(4-methylpentyl)cyclohexyl)ethyl)-4-trifluoromethoxybiphenyl Compound No. 132
2'-fluoro-4'-(2-(4-(4-methylpentyl)cyclohexyl)ethyl)-3-fluoro-4-trifluoromethoxybiphenyl Compound No. 133
2'-fluoro-4'-(2-(4-(4-methylpentyl)cyclohexyl)ethyl)-3,5-difluoro-4-trifluoromethoxybiphenyl Compound No. 134
2',6'-difluoro-4'-(2-(4-(4-methylpentyl)cyclohexyl)ethyl)-4-trifluoromethoxybiphenyl Compound No. 135
2',6'-difluoro-4'-(2-(4-(4-methylpentyl)cyclohexyl)ethyl)-3-fluoro-4-trifluoromethoxybiphenyl Compound No. 136
2',6'-difluoro-4'-(2-(4-(4-methylpentyl)cyclohexyl)ethyl)-3,5-difluoro-4-trifluoromethoxybiphenyl Compound No. 137
4-(2-(4-(4-(4-methylpentyl)cyclohexyl)cyclohexyl)ethyl)-1-trifluoromethoxybenzene Compound No. 138
4-(2-(4-(4-(4-methylpentyl)cyclohexyl)cyclohexyl)ethyl)-1-trifluoromethoxy2-fluorobenzene Compound No. 139
4-(2-(4-(4-(4-methylpentyl)cyclohexyl)cyclohexyl)ethyl)-1-trifluoromethoxy-2,6-difluorobenzene Compound No. 140
4-(2-(4-(4-(4-methylpentyl)cyclohexyl)phenyl)ethyl)-1-trifluoromethoxybenzene Compound No. 141
4-(2-(4-(4-(4-methylpentyl)cyclohexyl)phenyl)ethyl)-1-trifluoromethoxy-2-fluorobenzene Compound No. 142
4-(2-(4-(4-(4-methylpentyl)cyclohexyl)phenyl)ethyl)-1-trifluoromethoxy-2,6-difluorobenzene Compound No. 143
4-(2-(2-fluoro-4-(4-(4-methylpentyl)cyclohexyl)phenyl)ethyl)-1-trifluoromethoxybenzene Compound No. 144
4-(2-(2-fluoro-4-(4-(4-methylpentyl)cyclohexyl)phenyl)ethyl)-1-trifluoromethoxy-2-fluorobenzene Compound No. 145
4-(2-(2-fluoro-4-(4-(4-methylpentyl)cyclohexyl) phenyl)ethyl)-1-trifluoromethoxy-2,6-difluorobenzene Compound No. 146
4-(2-(2,6-difluoro-4-(4-(4-methylpentyl)cyclohexyl)phenyl)ethyl)-1-trifluoromethoxybenzene Compound No. 147
4-(2-(2,6-difluoro-4-(4-(4-methylpentyl)cyclohexyl)phenyl)ethyl)-1-trifluoromethoxy-2-fluorobenzene Compound No. 148
4-(2-(2,6-difluoro-4-(4-(4-methylpentyl)cyclohexyl)phenyl)ethyl)-1-trifluoromethoxy-2,6-difluorobenzene Compound No. 149
4'-(4-(5-methylhexyl)cyclohexyl)-4-trifluoromethoxybiphenyl S-I point 126.8° to 128.1° C.

Example 3 (Use Example 1)

Liquid crystal composition B1 comprising the following compounds was prepared:
(In Use Examples, "%" means "% by weight".)

| | |
|---|---|
| 4-(4-propylcyclohexyl)benzonitrile | 30% |
| 4-(4-pentylcyclohexyl)benzonitrile | 40% |
| 4-(4-heptylcyclohexyl)benzonitrile | 30% |

This nematic liquid crystal composition B1 had a clearing point of 52.3° C., threshold voltage of 1.60 V at a cell thickness of 9 μm, value of dielectric anisotropy of 10.7, value of refractive anisotropy of 0.119, and viscosity at 20° C. of 21.7 mPa.s. Liquid crystal composition B1 in an amount of 85 parts by weight and 15 parts by weight of a compound of the present invention, 4-(4-(4-(4-methylpentyl)cyclohexyl)cyclohexyl)-1-trifluoromethoxybenzene (Compound No. 113) were mixed to produce liquid crystal composition A1. This liquid crystal composition A1 had a clearing point of 57.1° C., threshold voltage of 1.55 V at a cell thickness of 8.7 μm, value of dielectric anisotropy of 8.2, value of refractive anisotropy of 0.77, and viscosity at 20° C. of 26.2 mPa-S. While this liquid crystal composition was left in a freezer at −20° C. for 60 days as it is, deposition of crystals was not observed. Further, voltage holding ratio (100° C. for 60 min) of the liquid crystal composition A1 was determined to be 99.8%.

Example 4 (Use Example 2)

| | |
|---|---|
| 4-(4-(4-(4-methylpentyl)cyclohexyl)cyclohexyl)-1-trifluoromethoxybenzene (Compound No. 113) | 1.0% |
| 4-(4-heptylcyclohexyl)-1-fluorobenzene | 4.0% |
| 4-(4-heptylcyclohexyl)-1,2-difluorobenzene | 4.0% |
| 4-(4-(4-ethylcyclohexyl)cyclohexyl)-1,2-difluorobenzene | 13.3% |
| 4-(4-(4-propylcyclohexyl)cyclohexyl)-1,2-difluorobenzene | 13.3% |
| 4-(4-(4-pentylcyclohexyl)cyclohexyl)-1,2-difluorobenzene | 13.3% |
| 4-(4-(2-(4-ethylcyclohexyl)ethyl)cyclohexyl)-1,2-difluorobenzene | 4.0% |
| 4-(4-(2-(4-propylcyclohexyl)ethyl)cyclohexyl)-1,2-difluorobenzene | 2.0% |
| 4-(4-(2-(4-pentylcyclohexyl)ethyl)cyclohexyl)-1,2-difluorobenzene | 4.0% |
| 4'-(4-ethylcyclohexyl)-3,4-difluorobiphenyl | 2.5% |
| 4'-(4-propylcyclohexyl)-3,4-difluorobiphenyl | 2.5% |
| 4'-(4-pentylcyclohexyl)-3,4-difluorobiphenyl | 5.0% |
| 4-(4-(4-propylcyclohexyl)cyclohexyl)-1-fluorobenzene | 9.0% |
| 4'-fluorobiphenyly1=4-(4-propylcyclohexyl)cyclohexanecarboxylate | 3.0% |
| 4-fluorophenyl=4-(4-pentylcyclohexyl)cyclohexanecarboxylate | 5.0% |
| 4-(2-(4-(4-propylcyclohexyl)cyclohexyl)ethyl)-1-trifluoromethoxybenzene | 3.0% |
| 4-(4-(4-propylcyclohexyl)cyclohexyl)-1-trifluoromethoxybenzene | 5.0% |
| 4-(2-(4-(4-propylcyclohexyl)cyclohexyl)ethyl)-1,2-difluorobenzene | 6.0% |

$T_{NI}$=110.3 [°C.]
$\eta$=22.4 [mPa.S]

Δn=0.086
Δε=4.5
Vth=2.43 [V]

Example 5 (Use Example 3)

| | |
|---|---|
| 4-(4-(4-methylpentyl)cyclohexyl)cyclohexyl)-1-trifluoromethoxybenzene (Compound No. 113) | 11.0% |
| 4-(4-heptylcyclohexyl)-1-fluorobenzene | 4.0% |
| 4-(4-heptylcyclohexyl)-1,2-difluorobenzene | 4.0% |
| 4-(4-(4-ethylcyclohexyl)cyclohexyl)-1,2-difluorobenzene | 10.0% |
| 4-(4-(4-propylcyclohexyl)cyclohexyl)-1,2-difluorobenzene | 10.0% |
| 4-(4-(4-pentylcyclohexyl)cyclohexyl)-1,2-difluorobenzene | 10.0% |
| 4-(4-(2-(4-ethylcyclohexyl)ethyl)cyclohexyl)-1,2 difluorobenzene | 4.0% |
| 4-(4-(2-(4-propylcyclohexyl)ethyl)cyclohexyl)-1,2-difluorobenzene | 2.0% |
| 4-(4-(2-(4-pentylcyclohexyl)ethyl)cyclohexyl)-1,2-difluorobenzene | 4.0% |
| 4'-(4-ethylcyclohexyl)-3,4-difluorobiphenyl | 2.5% |
| 4'-(4-propylcyclohexyl)-3,4-difluorobiphenyl | 2.5% |
| 4'-(4-pentylcyclohexyl)-3,4-difluorobiphenyl | 5.0% |
| 4-(4-(4-propylcyclohexyl)cyclohexyl)-1-fluorobenzene | 9.0% |
| 4'-fluorobiphenylyl-4-(propylcyclohexyl)cyclohexanecarboxylate | 3.0% |
| 4-fluorophenyl-4-(4-pentylcyclohhexyl)cyclohexanecarboxylate | 5.0% |
| 4-(2-(4-(4-propylcyclohexyl)cyclohexyl)ethyl-1-trifluoromethoxybenzene | 3.0% |
| 4-(4-(4-propylcyclohexyl)cyclohexyl)-1-trifluoromethoxybenzene | 5.0% |
| 4(2-(4-(4-propylcyclohexyl)cyclohexyl)ethyl)-1,2-difluorobenzene | 6.0% |

T<sub>NI</sub>=111.3 [°C.]
β=22.3 [mPa.S]
Δn=0.086
Δε=4.3
Vth=2.43 [V]

Example 6 (Use Example 4)

| | |
|---|---|
| 4'-(4-(5-methylhexyl)cyclohexyl)-4-trifluoromethoxybiphenyl (Compound No. 149) | 8.0% |
| 5-(4-heptylcyclohexyl)-1,2,3-trifluorobenzene | 5.0% |
| 4'-(4-propylcyclohexyl)-3,4,5-trifluorobiphenyl | 8.0% |
| 4'-(4-pentylcyclohexyl)-3,4,5-trifluorobiphenyl | 2.0% |
| 5-(4-(4-propylcyclohexyl)cyclohexyl)-1,2,3-trifluorobenzene | 7.0% |
| 5-(4-(4-butylcyclohexyl)cyclohexyl)-1,2,3-trifluorobenzene | 5.0% |
| 5-(2-(4-(4-propylcyclohexyl)cyclohexyl)ethyl)-1,2,3-trifluorobenzene | 10.0% |
| 5-(2-(4-(4-pentylcyclohexyl)cyclohexyl)ethyl)-1,2,3-trifluorobenzene | 5.0% |
| 5-(4-(2-(4-propylcyclohexyl)ethyl)cyclohexyl)-1,2,3-trifluorobenzene | 10.0% |
| 5-(4-(2-(4-butylcyclohexyl)ethyl)cyclohexyl)-1,2,3-trifluorobenzene | 10.0% |
| 5-(4-(2-(4-pentylcyclohexyl)ethyl)cyclohexyl)-1,2,3-trifluorobenzene | 10.0% |
| 3,4,5-trifluorophenyl-4-(4-propylcyclohexyl)cyclohexanecarboxylate | 8.0% |
| 3,4,5-trifluorophenyl-4-(4-butylcyclohexyl)cyclohexanecarboxylate | 3.0% |
| 3,4,5-trifluorophenyl-4-(4-pentylcyclohexyl)cyclohexanecarboxylate | 3.0% |
| 4'-(4-(4-ethylcyclohexyl)cyclohexyl)-3,4,5-trifluorobiphenyl | 2.0% |
| 3,4,5-trifluorophenyl-4-(4-propylcyclohexyl)benzoate | 2.0% |
| 3,4,5-trifluorophenyl-4-(4-pentylcyclohexyl)benzoate | 2.0% |

T<sub>NI</sub>=79.4 [°C.]
η=29.0 [mPa.S]
Δn=0.084
Δε=8.9
Vth=1.54 [V]

Example 7 (Use Example 5)

| | |
|---|---|
| 4'-(4-(5-methylhexyl)cyclohexyl)-4-trifluoromethoxybiphenyl (Compound No. 149) | 4.0% |
| 4-(4-(4-methylpentyl)cyclohexyl)cyclohexyl)-1-trifluoromethoxybenzene (Compound No. 113) | 1.0% |
| 4-(4-propylcyclohexyl)-1-chlorobenzene | 4.0% |
| 4-(4-pentylcyclohexyl)-1-chlorobenzene | 4.0% |
| 4-(4-heptylcyclohexyl)-1-chlorobenzene | 5.0% |
| 4'-4-(ethylcyclohexyl)-3,4-difluorobiphenyl | 7.5% |
| 4'-4-(propylcyclohexyl)-3,4-difluorobiphenyl | 7.5% |
| 4'-4-(pentylcyclohexyl)-3,4-difluorobiphenyl | 15.0% |
| 4-(4-ethylcyclohexyl)cyclohexyl)-1-chlorobenzene | 6.0% |
| 4-(4-propylcyclohexyl)cyclohexyl)-1-chlorobenzene | 10.0% |
| 4-(4-butylcyclohexyl)cyclohexyl)-1-chlorobenzene | 10.0% |
| 4'-(4-propylcyclohexyl)-3,4,5-trifluorobiphenyl | 12.0% |
| 4'-(4-pentylcyclohexyl)-3,4,5-trifluorobiphenyl | 14.0% |

T<sub>NI</sub>=93.8 [°C.]
η=24.0 [mPa.S]
Δn=0.125
Δε=6.0
Vth=2.10 [V]

Example 8 (Use Example 6)

| | |
|---|---|
| 4'-(4-(2-methylpropyl)cyclohexyl)-4-trifluoromethoxybiphenyl (Compound No. 1) | 4.0% |
| 4'-(4-(2-methylbutyl)cyclohexyl)-4-trifluoromethoxybiphenyl (Compound No. 2) | 4.0% |
| 4'-(4-(2-methylpentyl)cyclohexyl)-4-trifluoromethoxybiphenyl (Compound No. 80) | 4.0% |
| 4'-(4-(5-methylhexyl)cyclohexyl)-4-trifluoromethoxybiphenyl (Compound No. 149) | 4.0% |
| 4'-(4-(3-methylpentyl)cyclohexyl)-4-trifluoromethoxybiphenyl (Compound No. 44) | 4.0% |
| 4-(4-(4-methylpentyl)cyclohexyl)cyclohexyl)-1-trifluoromethoxybenzene (Compound No. 113) | 1.0% |
| 4-(4-propylcyclohexyl)-1-chlorobenzene | 4.0% |
| 4-(4-pentylcyclohexyl)-1-chlorobenzene | 4.0% |
| 4-(4-heptylcyclohexyl)-1-chlorobenzene | 5.0% |
| 4'-(4-ethylcyclohexyl)-3,4'-difluorobiphenyl | 3.5% |
| 4'-(4-propylcyclohexyl)-3,4'-difluorobiphenyl | 3.5% |
| 4'-(4-pentylcyclohexyl)-3,4'-difluorobiphenyl | 7.0% |
| 4-(4-(4-ethylcyclohexyl)cyclohexyl)-1-chlorobenzene | 6.0% |
| 4-(4-(4-propylcyclohexyl)cyclohexyl)-1-chlorobenzene | 10.0% |
| 4-(4-(4-butylcyclohexyl)cyclohexyl)-1-chlorobenzene | 10.0% |
| 4'-(4-propylcyclohexyl)-3,4,5-trifluorobiphenyl | 12.0% |
| 4'-(4-pentylcyclohexyl)-3,4,5-trifluorobiphenyl | 14.0% |

T<sub>NI</sub>=92.5 [°C.]
η=23.1 [mPa.S]
Δn=0.123
Δε=6.0
Vth=2.10 [V]

Example 9 (Use Example 7)

| | |
|---|---|
| 4'-(4-(5-methylhexyl)cyclohexyl)-4-trifluoromethoxybiphenyl (Compound No. 149) | 3.0% |
| 4-(4-(3-butenyl)cyclohexyl)benzonitrile | 10.0% |
| 4-(4-(3-pentenyl)cyclohexyl)benzonitrile | 10.0% |
| 4-(4-propylcyclohexyl)benzonitrile | 14.0% |
| 4-(4-methoxymethylcyclohexyl)benzonitrile | 8.0% |
| 4-(4-ethoxymethylcyclohexyl)benzonitrile | 4.0% |
| 4-(4-(4-propylcyclohexyl)cyclohexyl)benzonitrile | 4.0% |
| 4'-propyl-4-butylbicyclohexane | 6.0% |
| 4'-vinyl-4-butylbicyclohexane | 4.0% |
| 4'-methoxymethyl-4-pentylbicyclohexane | 8.0% |
| 4-(2-(4-ethylphenyl)ethynyl)-1-methoxybenzene | 11.0% |

-continued

| | |
|---|---|
| 4-(4-(4-propylcyclohexyl)cyclohexyl)-1-ethylbenzene | 4.0% |
| 4-(4-(4-propylcyclohexyl)cyclohexyl)-1-propylbenzene | 6.0% |
| 4-(4-(4-vinylcyclohexyl)cyclohexyl)-1-methylbenzene | 4.0% |
| 4-(4-(4-propylcyclohexyl)cyclohexyl)-1-methylbenzene | 4.0% |

$T_{NI}$=72.1 [°C.]
η=17.9 [mPa.S]
Δn=0.124
Δε=7.7
Vth=1.75 [V]

Example 10 (Use Example 8)

| | |
|---|---|
| 4'-(4-(5-methylhexyl)cyclohexyl)-4-trifluoromethoxybiphenyl (Compound No. 149) | 3.0% |
| 3,5-difluoro-4-cyanophenyl=4-(4-pentenyl)benzoate | 12.0% |
| 3-fluoro-4-cyanophenyl=4-ethoxyethylbenzoate | 6.0% |
| 3-fluoro-4-cyanophenyl=4-propoxyethylbenzoate | 8.0% |
| 4-(4-propylcyclohexyl)-3-fluoro-4-cyanobenzene | 16.0% |
| 4'-propyl-4-pentylbicyclohexane | 8.0% |
| 4'-propyl-4-methoxymethylbicyclohexane | 4.0% |
| 4-(2-(4-butylphenyl)ethynyl)-1-ethoxybenzene | 6.0% |
| 4-(2-(4-ethylphenyl)ethynyl)-1-methylbenzene | 1.0% |
| 4-(2-(4-methylphenyl)ethynyl)-1-hexylbenzene | 2.0% |
| 4-(2-(4-butylphenyl)ethynyl)-1-butylbenzene | 1.0% |
| 4-(4-(4-ethylcyclohexyl)cyclohexyl)-2-fluorobenzonitrile | 9.0% |
| 4-(4-(4-propylcyclohexyl)cyclohexyl)-2-fluorobenzonitrile | 8.0% |
| 4-(2-(4-(2-(4-propylcyclohexyl)ethyl)phenyl)ethynyl)-1-ethylbenzene | 3.0% |
| 4-(2-(4-(2-(4-propylcyclohexyl)ethyl)phenyl)ethynyl)-1-propylbenzene | 3.0% |
| 4-(2-(4-(2-(4-propylcyclohexyl)ethyl)phenyl)ethynyl)-1-butylbenzene | 3.0% |
| 4-(2-(2-fluoro-4-(4-propylcyclohexyl)phenyl)ethynyl)-1-propylbenzene | 4.0% |
| 4'-(4-methoxymethylcyclohexyl)-4-pentylcyclohexylbiphenyl | 3.0% |

$T_{NI}$=74.1 [°C.]
η=37.0 [mPa.S]
Δn=0.150
Δε=23.4
Vth=0.96 [V]

What is claimed is:

1. A liquid crystalline compound expressed by the following general formula (1)

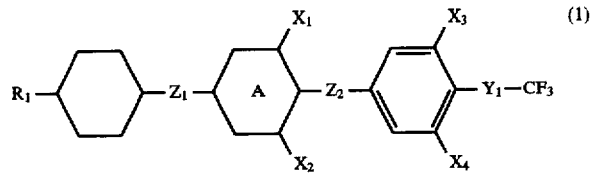

wherein $R_1$ represents a branched alkyl group having 3 to 10 carbon atoms, ring A represents a 1,4-phenylene group or 1,4-cyclohexylene group, $Z_1$ and $Z_2$ independently represent a single bond or 1,2-ethylene group, respectively, $X_1$, $X_2$, $X_3$, and $X_4$ independently represent a fluorine atom or hydrogen atom, respectively, provided that at least one of $X_1$, $X_2$, $X_3$ and $X_4$ is a fluorine atom, and $Y_1$ represents an oxygen atom or a single bond.

2. The liquid crystalline compound according to claim 1 wherein $R_1$ is 4-methylpentyl group.

3. The liquid crystalline compound according to claim 1 wherein $R_1$ is 3-methylpentyl group.

4. The liquid crystalline compound according to claim 1 wherein $R_1$ is 3-methylbutyl group.

5. The liquid crystalline compound according to claim 1 wherein $R_1$ is 2-methylpropyl group.

6. The liquid crystalline compound according to claim 1 wherein $R_1$ is 5-methylhexyl group.

7. A liquid crystal composition comprising at least two components and containing at least one liquid crystalline compound expressed by the general formula (1) defined in claim 1.

8. A liquid crystal composition containing, as the first component, at least one compound defined in any one of claims 1 to 6 and containing, as the second component, at least one compound selected from the group consisting of the compounds expressed by the general formula (2), (3), or (4)

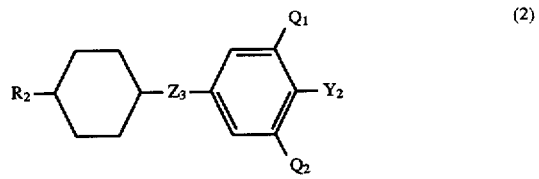

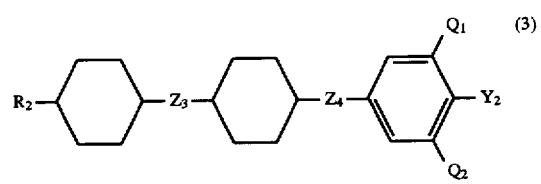

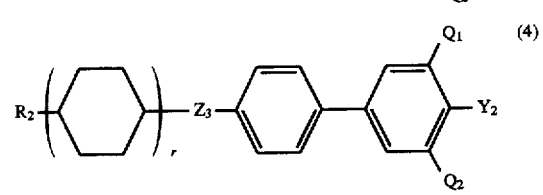

wherein $R_2$ represents an alkyl group having 1 to 10 carbon atoms, Y2 represents fluorine atom or chlorine atom, $Q_1$ and $Q_2$ independently represent fluorine atom or hydrogen atom, respectively, r represents 1 or 2, and $Z_3$ and $Z_4$ independently represent —$CH_2CH_2$— or a single bond.

9. A liquid crystal composition containing, as the first component, at least one compound defined in any one of claims 1 to 6 and containing, as the second component, at least one compound selected from the group consisting of the compounds expressed by the general formula (5), (6), (7), (8), or (9)

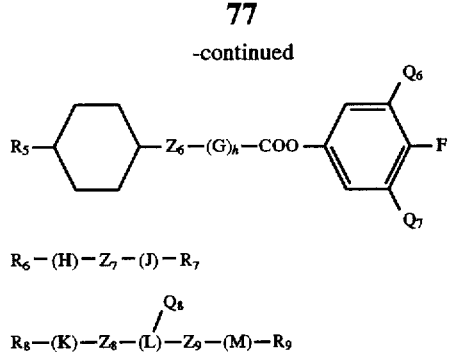

$R_6—(H)—Z_7—(J)—R_7$ (8)

$R_8—(K)—Z_8—(L)—Z_9—(M)—R_9$ with $Q_8$ branch (9)

wherein $R_3$ represents an alkyl group having 1 to 10 carbon atoms or an alkenyl group having 2 to 10 carbon atoms, in either case, any methylene group (—$CH_2$—) may be replaced by oxygen atom (—O—), but in neither case are two or more consecutive carbon atoms replaced by oxygen atom consecutively, $Z_5$ represents —$CH_2CH_2$—, —COO—, or a single boned, $Q_3$ and $Q_4$ independently represent fluorine atom or hydrogen atom, (E) represents cyclohexane ring, benzene ring, or 1,3-dioxane ring, and s represents 0 or 1.

$R_4$ represents an alkyl group having 1 to 10 carbon atoms, $Q_5$ represents fluorine atom or hydrogen atom, and k represents 0 or 1.

$R_5$ represents an alkyl group having 1 to 10 carbon atoms, (G) represents cyclohexane ring or benzene ring, $Q_6$ and $Q_7$ independently represent fluorine atom or hydrogen atom, $Z_6$ represents —COO— or a single bond, add h represents 0 or 1.

$R_6$ and $R_7$ independently represent an alkyl group, alkyloxy group, or alkyloxymethyl group each having 1 to 10 carbon atoms, (H) represents cyclohexane ring, pyrimidine ring, or benzene ring, (J) represents cyclohexane ring or benzene ring, $Z_7$ represents —C≡C—, —COO—, —$CH_2CH_2$—, or a single bond.

$R_8$ represents an alkyl group or alkoxyl group each having 1 to 10 carbon atoms, $R_9$ represents an alkyl group, alkyloxy group, or alkoxymethyl group each having 1 to 10 carbon atoms, (K) represents cyclohexane ring or pyrimidine ring, (L) and (M) independently represent cyclohexane ring or benzene ring, $Z_8$ represents —COO—, —$CH_2CH_2$—, or a single bond, $Z_9$ represents —C≡C—, —COO—, or a single bond, and $Q_8$ represents fluorine atom or hydrogen atom.

10. A liquid crystal display device having used a liquid crystal composition comprising at least two components and containing at least one compound expressed by the general formula (1) define in claim 1.

11. A liquid crystal display device having a liquid crystal composition defined in claim 8.

12. A liquid crystal display device having a liquid crystal composition defined in claim 9.

13. The liquid crystalline compound according to claim 1 wherein $X_3$ represents a fluorine atom.

* * * * *